(12) United States Patent
Zhang et al.

(10) Patent No.: US 10,227,622 B2
(45) Date of Patent: Mar. 12, 2019

(54) HOST CELL MODIFIED TO PRODUCE 2-PYRROLIDONE

(71) Applicant: The Regents of the University of California, Oakland, CA (US)

(72) Inventors: Jingwei Zhang, Fullerton, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/099,488

(22) Filed: Apr. 14, 2016

(65) Prior Publication Data

US 2016/0304922 A1  Oct. 20, 2016

Related U.S. Application Data

(60) Provisional application No. 62/147,461, filed on Apr. 14, 2015.

(51) Int. Cl.
| | | |
|---|---|---|
| *C12N 9/16* | (2006.01) | |
| *C12N 9/88* | (2006.01) | |
| *C12N 9/78* | (2006.01) | |
| *C12N 15/54* | (2006.01) | |
| *C12P 17/10* | (2006.01) | |
| *C12N 15/52* | (2006.01) | |
| *C12N 9/00* | (2006.01) | |

(52) U.S. Cl.
CPC ............... *C12P 17/10* (2013.01); *C12N 9/88* (2013.01); *C12N 9/93* (2013.01); *C12N 15/52* (2013.01); *C12Y 401/01015* (2013.01)

(58) Field of Classification Search
CPC ... C12N 9/78; C12N 9/88; C12N 9/16; C12Y 302/01004; C12Y 111/01016; C12Y 401/02; C12P 17/10; C12P 17/188
USPC ...... 435/196, 233, 191, 252.35, 69.1, 252.3, 435/232, 320.1
See application file for complete search history.

(56) References Cited

U.S. PATENT DOCUMENTS 7,375,088 B2  5/2008 Bachmann et al.

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Takahashi et al., "Robust production of gamma-amino butyric acid using recombinant Corynebacterium glutamicum expressing glutamate decarboxylase from *Escherichia coli*." Enzyme Microb Technol 51(3): 171-176 (2012).
Tran et al., "Insights into protein-protein and enzyme-substrate interactions in modular polyketide synthases." Chem Biol 17(7): 705-716 (2010).
Weissman et al., "Protein-protein interactions in multienzyme megasynthetases." Chembiochem 9(6): 826-848 (2008).
Zhang et al., "A Three Enzyme Pathway for 2-Amino-3-hydroxycyclopent-2-enone Formation and Incorporation in Natural Product Biosynthesis." J. Am. Chem. Soc. 132: 6402-6411 (2010).
Wong et al., "Protein-protein recognition between acyltransferases and acyl carrier proteins in multinodular polyketide synthases." Biochemistry 49(1): 95-102 (2010).
Yadav et al., "Towards prediction of metabolic products of polyketide synthases: an in silico analysis." PLoS Comput Biol 5(4): e1000351 (2009).
Zazopoulos et al., "A genomics-guided approach for discovering and expressing cryptic metabolic pathways." Nat Biotechnol 21(2): 187-190 (2003).
Biase et al., "The response to stationary-phase stress conditions in *Escherichia coli*: role and regulation of the glutamic acid decarboxylase system." Molecular Microbiology 32(6): 1198-1211 (1999).
Moore et al., "Biosynthesis and attachment of novel bacterial polyketide synthase starter units." Nat Prod Rep 19(1): 70-99 (2002).
Harreus, et al., "2-pyrrolidone." Ullmann's Encyclopedia of Industrial Chemistry, Wiley-VCH Verlag GmbH & Co. KGaA, Weinheim (2011).
Amin, et al., "Prediction and experimental validation of enzyme substrate specificity in protein structures." Proc Natl Acad Sci U S A 110(45): E4195-4202 (2013).
Baba, et al., "Construction of *Escherichia coli* K-12 in-frame, single-gene knockout mutants: the Keio collection." Mol Syst Biol 2 (2006).
Bachmann, B. O., "Biosynthesis: is it time to go retro?" Nat Chem Biol 6(6): 390-393 (2010).
Bachmann, et al., "Polyene polyketides, processes for their production and their use as a pharmaceutical", Ecopia Biosciences Inc., (2008). https://patents.google.com/patent/US20050187167/en17.
Basf, "2-Pyrrolidone." Retrieved Mar. 5, 2015,from the webpage of: basf.ca/group/corporate/ca/en/brand/2_PYRROLIDONE (2015).
Bernal, et al., "Role of betaine:CoA ligase (CaiC) in the activation of betaines and the transfer of coenzyme A in *Escherichia coli*." Journal of Applied Microbiol 105(1): 42-50 (2008).
Capitani, et al., "Crystal structure and functional analysis of *Escherichia coli* glutamate decarboxylase." EMBO J. 22 (16): 4027-4037 (2003).
Chaitan, Khosla, J. D. K. "Metabolic engineering for drug discovery and development." Nature Reviews | Drug Discovery 2: 1019 (2003).
Chang, A., et al., "BRENDA in 2015: exciting developments in its 25th year of existence." Nucleic Acids Res 43 (Database issue): D439-446 (2015).
Dietrich, et al., "High-throughput metabolic engineering: advances in small-molecule screening and selection." Annu Rev Biochem 79: 563-590 (2010).

(Continued)

*Primary Examiner* — Robert B Mondesi
*Assistant Examiner* — Mohammad Y Meah
(74) *Attorney, Agent, or Firm* — Robin C. Chiang; Lawrence Berkeley National Laboratory

(57) ABSTRACT

The present invention provides for a genetically modified host cell comprising a 2-pyrrolidone synthase, or an enzymatically active fragment thereof, heterologous to the host cell.

17 Claims, 15 Drawing Sheets

Specification includes a Sequence Listing.

(56) References Cited

OTHER PUBLICATIONS

Doughtery, et al., "Directed evolution: new parts and optimized function." Curr Opin Biotechnol 20(4): 486-491 (2009).
Du, et al., "PKS and NRPS release mechanisms." Nat Prod Rep 27(2): 255-278 (2010).
Du, et al., "Hybrid peptide-polyketide natural products: biosynthesis and prospects toward engineering novel molecules." Metab Eng 3(1): 78-95 (2001).
Dutta, et al., "Structure of a modular polyketide synthase." Nature 510(7506): 512-517 (2014).
Esvelt, et al., "A system for the continuous directed evolution of biomolecules." Nature 472(7344): 499-503 (2011).
Fluitt, et al., "Ribosome kinetics and aa-tRNA competition determine rate and fidelity of peptide synthesis." Comput Biol Chem 31(5-6): 335-346 (2007).
Galperin, et al., "Divergence and convergence in enzyme evolution." J Biol Chem 287(1): 21-28 (2012).
McAlpine, James B., "Microbial Genomics as a Guide to Drug Discovery and Structural Elucidation: ECO-02301, a Novel Antifungal Agent, as an Example." J. Nat. Prod.(68): 493-496 (2005).
Kalaitzis, et al., "In vitro biosynthesis of unnatural enterocin and wailupemycin polyketides." J Nat Prod 72(3): 469-472 (2009).
Nishihara, et al., "Overexpression of Trigger Factor Prevents Aggregation of Recombinant Proteins in *Escherichia coli*." Appl Environ Microbiol 66(3): 884-889 (2000).
Nishihara, et al., "Chaperone Coexpression Plasmids: Differential and Synergistic Roles of DnaK-DnaJ-GrpE and GroEL-GroES in Assisting Folding of an Allergen of Japanese Cedar Pollen, Cryj2, in *Escherichia coli*." Appl Environ Microbiol 64(5): 1694-1699 (1998).
Khosla, et al., "Revisiting the modularity of modular polyketide synthases." Curr Opin Chem Biol 13(2): 135-143 (2009).
Kizer, et al., "Application of functional genomics to pathway optimization for increased isoprenoid production." Appl Environ Microbiol 74(10): 3229-3241 (2008).
Vo et al., "Effects of glutamate decarboxylase and gamma-aminobutyric acid (GABA) transporter on the bioconversion of GABA in engineered *Escherichia coli*." Bioprocess Biosyst Eng 35(4): 645-650 (2012).
Li et al., "Analysis of the indanomycin biosynthetic gene cluster from Streptomyces antibioticus NRRL 8167." Chembiochem 10(6): 1064-1072 (2009).
Li et al., "Biosynthesis of the unique amino acid side chain of butirosin: possible protective-group chemistry in an acyl carrier protein-mediated pathway." Chem Biol 12(6): 665-675 (2005).
Llewellyn et al., "Biosynthesis of butirosin: transfer and deprotection of the unique amino acid side chain." Chem Biol 14(4): 379-386 (2007).
Lohr, L. J. "The System of 2-pyrrolidone-water." J. Phys. Chem. 62 (9): 1150-1151 (1958).
Ma et al., "Structure and mechanism of a glutamate-GABA antiporter." Nature 483(7391): 632-636 (2012).
Medema et al., "Synthetic biology in Streptomyces bacteria." Methods Enzymol 497: 485-502 (2011).
Menzella et al., "Combinatorial polyketide biosynthesis by de novo design and rearrangement of modular polyketide synthase genes." Nat Biotechnol 23(9): 1171-1176 (2005).
Moon, T. S. "Retrobiosynthesis of D-Glucaric Acid in a Metabolically Engineered Strain of *Escherichia coli*." Department of Chemical Engineering, Massachusetts Institute of Technology. Doctor of Philosophy in Chemical Engineering: 181 (2009).
Ogasawara et al., "Cloning, sequencing, and functional analysis of the biosynthetic gene cluster of macrolactam antibiotic vicenistatin in Streptomyces halstedii." Chem Biol 11(1): 79-86 (2004).
Pirilaa et al., "structure of 2-pyrrolidone monohydrate." Z. Naturforsch. 54b: 1598-1601 (1999).
Park et al., "Synthesis of nylon 4 from gamma-aminobutyrate (GABA) produced by recombinant *Escherichia coli*." Bioprocess Biosyst Eng 36(7): 885-892 (2013).
Pennacchietti et al., "Mutation of His465 alters the pH-dependent spectroscopic properties of *Escherichia coli* glutamate decarboxylase and broadens the range of its activity toward more alkaline pH." J Biol Chem 284(46): 31587-31596 (2009).
Proshkin et al., "Cooperation between translating ribosomes and RNA polymerase in transcription elongation." Science 328(5977): 504-508 (2010).
Sakuda et al., "Novel linear polyene antibiotics: linearmycins." Journal of the Chemical Society, Perkin Transactions 1(18): 2315 (1996).
Shi et al., "Enhancement of gamma-aminobutyric acid production in recombinant Corynebacterium glutamicum by co-expressing two glutamate decarboxylase genes from Lactobacillus brevis." J Ind Microbiol Biotechnol 40(11): 1285-1296 (2013).
Shinohara et al., "A natural protecting group strategy to carry an amino acid starter unit in the biosynthesis of macrolactam polyketide antibiotics." J Am Chem Soc 133(45): 18134-18137 (2011).
Shiue et al., "Improving D-glucaric acid production from myo-inositol in *E. coli* by increasing MIOX stability and myoinositol transport." Metab Eng 22: 22-31 (2014).
Siller et al., "Slowing bacterial translation speed enhances eukaryotic protein folding efficiency." J Mol Biol 396(5): 1310-1318 (2010).
Simunovic et al., "Myxovirescin A biosynthesis is directed by hybrid polyketide synthases/nonribosomal peptide synthetase, 3-hydroxy-3-methylglutaryl-CoA synthases, and trans-acting acyltransferases." Chembiochem 7(8): 1206-1220 (2006).
Stavila et al., "Synthesis of lactams using enzyme-catalyzed aminolysis." Tetrahedron Letters 54(5): 370-372 (2013).
Studier, F. W. "Protein production by auto-induction in high-density shaking cultures." Protein Expr Purif 41(1): 207-234 (2005).
Werpy, G. P. "Top Value Added chemicals from Biomass." vol. I—results of screening for potential candidates from sugars and synthesis gas (2004).
Ruusala et al., "Hyper-accurate ribososomes inhibit growth." The EMBO Journal 3(11): 2575-2580 (1984).
Farnet et al., "Improving Drug Discovery From Microorganisms," Natural Products, Part II, pp. 95-106 (2005).

\* cited by examiner

SEQUENCE LISTING

```
<160> NUMBER OF SEQ ID NOS: 14

<210> SEQ ID NO 1
<211> LENGTH: 470
<212> TYPE: PRT
<213> ORGANISM: Streptomyces aizunensis

<400> SEQUENCE: 1

Met Arg Pro Met Thr Ala Lys Ile Phe Ala Val Asp Ser Val Arg Pro
1               5                   10                  15

Ile Asp Glu Phe Glu Gln Asp Ala Leu Arg Val Ala Asp Val Ile Arg
            20                  25                  30

Glu Arg Gly Val Cys Leu Gly Asp Arg Val Met Leu Lys Ala Gly Asn
        35                  40                  45

Ser Ala Ser Tyr Val Cys Val Leu Tyr Ala Leu Met His Ile Gly Ala
    50                  55                  60

Ser Ile Val Leu Val Asp Gln Gln Glu His Lys Glu Glu Thr Arg Arg
65                  70                  75                  80
```

Ile Ala Leu Arg Thr Gly Val Lys Val Thr Phe Val Asp Asp Glu Thr
                85                  90                  95

Pro Ile Asp Gln Asp Ala Asp Pro Ile His Leu Tyr Glu Leu Met Val
            100                 105                 110

Ala Thr Gln Asn Arg Pro Pro Met Asp Ser Ala Leu Ser Phe Asp Ala
        115                 120                 125

Trp Gly Glu Leu Ser Asp Gly Leu Ile Met Trp Thr Ser Gly Ser Thr
130                 135                 140

Gly Ser Pro Lys Gly Val Val Lys Ser Gly Gly Lys Phe Leu Ala Asn
145                 150                 155                 160

Leu Arg Arg Asn Ala His Gln Val Gly His Arg Pro Asp Asp Val Leu
                165                 170                 175

Met Pro Leu Leu Pro Phe Ala His Gln Tyr Gly Leu Ser Met Val Leu
            180                 185                 190

Ile Ala Trp Leu Thr Arg Cys Ser Leu Val Ile Ala Pro Tyr Arg Arg
        195                 200                 205

Leu Asp Arg Ala Leu Arg Met Ala Arg Asp Ser Gly Thr Thr Val Ile
210                 215                 220

Asp Ala Thr Pro Ser Ser Tyr Arg Ser Ile Leu Gly Leu Val Thr Arg
225                 230                 235                 240

Lys Pro Ala Leu Arg Ala His Leu Ala Gly Thr Arg Met Phe Cys Val
                245                 250                 255

Gly Ala Ala Pro Leu Asp Ala Pro Leu Val Glu Ser Tyr Val Gln Glu
            260                 265                 270

Phe Gly Leu Pro Leu Leu Asp Ser Tyr Gly Ser Thr Glu Leu Asn Asn
        275                 280                 285

Ile Ala Phe Ala Thr Leu Asp Asn Pro Val Ser Cys Gly Arg Ala Met
290                 295                 300

Glu Gly Ile Gly Leu Arg Ile Val Asp Glu Asp Gly Arg Glu Val Ala
305                 310                 315                 320

Ala Gly Gln Pro Gly Glu Ile Glu Val Asp Thr Pro Asp Ala Leu Glu
                325                 330                 335

Gly Gln Ile Ala Glu Asp Gly Ser Ile Ile Pro Ala Pro Thr Gly Trp
            340                 345                 350

Gln Arg Thr Gly Asp Leu Gly His Leu Asp Ala Asp Gly Asn Leu Tyr
        355                 360                 365

Val Leu Gly Arg Lys Phe Ala Val His Arg Met Gly Tyr Thr Leu Tyr
370                 375                 380

Pro Glu Leu Ile Glu Arg Lys Val Ala Ala Glu Gly Cys Pro Thr Arg
385                 390                 395                 400

Ile Val Pro Leu Pro Asp Glu Leu Arg Gly Ser Gln Leu Val Phe Phe
                405                 410                 415

Val Glu Asp Asp Glu Gln Arg Asp Ala Gly Tyr Trp Arg Glu Arg Leu
            420                 425                 430

Cys Gly Leu Leu Pro Ala Phe Glu Gln Pro Asn Lys Val Val Val Leu
        435                 440                 445

Glu Gln Phe Pro Leu Asn Arg Asn Gly Lys Pro Asp Lys Lys Glu Leu
450                 455                 460

Thr Arg Met Ala Ala Glu
465                 470

<210> SEQ ID NO 2
<211> LENGTH: 41

<212> TYPE: DNA
<213> ORGANISM: Streptomyces aizunensis

<400> SEQUENCE: 2
gcgcgccatg ggcatgcgcc caatgaccgc taaaatcttc g                    41

<210> SEQ ID NO 3
<211> LENGTH: 33
<212> TYPE: DNA
<213> ORGANISM: Streptomyces aizunensis

<400> SEQUENCE: 3
gcgcgctcga gttctgccgc catacgggtc agc                             33

<210> SEQ ID NO 4
<211> LENGTH: 60
<212> TYPE: DNA
<213> ORGANISM: Streptomyces aizunensis

<400> SEQUENCE: 4
gcgcggaatt caaagatct tttaagaagg agatatacat atgggcagca gccatcatca  60

<210> SEQ ID NO 5
<211> LENGTH: 40
<212> TYPE: DNA
<213> ORGANISM: Streptomyces aizunensis

<400> SEQUENCE: 5
gcgcgctcga gtttggatcc tcattctgcc gccatacggg                      40

<210> SEQ ID NO 6
<211> LENGTH: 29
<212> TYPE: DNA
<213> ORGANISM: Escherichia coli

<400> SEQUENCE: 6
gcgcgcatat ggataagaag caagtaacg                                  29

<210> SEQ ID NO 7
<211> LENGTH: 35
<212> TYPE: DNA
<213> ORGANISM: Escherichia coli

<400> SEQUENCE: 7
gcgcgggatc cttatcaggt atgtttaaag ctgtt                           35

<210> SEQ ID NO 8
<211> LENGTH: 30
<212> TYPE: DNA
<213> ORGANISM: Escherichia coli

<400> SEQUENCE: 8
gcgcgcatat gggttcacgt tttggtgcga                                 30

<210> SEQ ID NO 9
<211> LENGTH: 43
<212> TYPE: DNA
<213> ORGANISM: Escherichia coli

<400> SEQUENCE: 9
gcgcgggatc cttatcaggt agctttaaag ctgttctgtt ggg                  43

<210> SEQ ID NO 10

```
<211> LENGTH: 37
<212> TYPE: DNA
<213> ORGANISM: Escherichia coli

<400> SEQUENCE: 10
gcgcgggatc cttatcattt aaagctgttc tgttggg                      37

<210> SEQ ID NO 11
<211> LENGTH: 60
<212> TYPE: DNA
<213> ORGANISM: Escherichia coli

<400> SEQUENCE: 11
gcgcgaattc aaaagatctt ttaagaagga gatatacata tggatagagg tgcaatggat    60

<210> SEQ ID NO 12
<211> LENGTH: 51
<212> TYPE: DNA
<213> ORGANISM: Escherichia coli

<400> SEQUENCE: 12
gcgcgctcga gtttggatcc ttatttcaga ttctttctaa ttattttccc c            51

<210> SEQ ID NO 13
<211> LENGTH: 24
<212> TYPE: DNA
<213> ORGANISM: Streptomyces aizunensis

<400> SEQUENCE: 13
gaattcaaaa gatctaggag gcat                                    24

<210> SEQ ID NO 14
<211> LENGTH: 18
<212> TYPE: DNA
<213> ORGANISM: Streptomyces aizunensis

<400> SEQUENCE: 14
taaggatcca aactcgag                                          18
```

HOST CELL MODIFIED TO PRODUCE 2-PYRROLIDONE

CROSS-REFERENCE TO RELATED APPLICATIONS

This application claims priority to U.S. Provisional Patent Application Ser. No. 62/147,461, filed on Apr. 14, 2015, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of microbial production of 2-pyrrolidone.

BACKGROUND OF THE INVENTION

2-Pyrrolidone was identified by the US Department of Energy as an important C4 "Top Value-Added Chemical from Biomass" that can potentially be derived from glutamate (T. Werpy 2004). 2-Pyrrolidone is currently used as precursor for the production of N-vinylpyrrolidone, a solvent for animal injection, a building block for active pharmaceutical ingredients, optical co-solvent for water-based ink formulation, process solvent for membrane filters and a copolymer for floor polish (BASF 2015). Potential applications include ring-opening polymerization of 2-pyrrolidone to form nylon-4, a fiber material with better thermal stability and the highest hydrophilicity in the nylon family of materials (Park, Kim et al. 2013). With a variety of applications, 2-pyrrolidone continues to be a product of huge commercial interest.

Current industrial production of 2-pyrrolidone involves the dehydrogenation of 1,4-butanediol (~$1,800-$2,000/ton) to form γ-butyrolactone on a copper catalyst (180-240° C.), followed by reacting aqueous γ-butyrolactone with ammonia on a magnesium silicate catalyst (250-290° C., 0.4-1.4 MPa) (FIG. 1A) (Albrecht Ludwig Harreus 2011). By using low cost glutamate ($900/ton) as starting material, as well as avoiding expensive catalysts and harsh reaction conditions, biological production of 2-pyrrolidone offers the potential for a cheaper and more environmentally friendly synthesis route. The ability to crystalize 2-pyrrolidone monohydrate at around 30° C. has the potential to enable low-cost separation of 2-pyrrolidone from fermentation media (Lohr 1958, Päivi Pirilaä 1999).

SUMMARY OF THE INVENTION

The present invention provides for a genetically modified host cell comprising a 2-pyrrolidone synthase, or an enzymatically active fragment thereof, heterologous to the host cell. In some embodiments, the 2-pyrrolidone synthase is *Streptomyces aizunensis* 2-pyrrolidone synthase or ORF27, or any enzyme capable of catalyzing the following reaction (1):

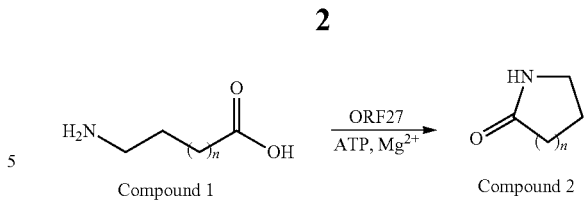

The present invention provides for a method of producing a Compound 2 in a genetically modified host cell. The method comprises culturing the genetically modified host cell in a medium under a suitable condition such that the culturing results in the genetically modified host cell producing a Compound 2. The host cell comprises an enzyme capable of catalyzing a Compound 1 into the Compound 2. In some embodiments, the method further comprises introducing one or more nucleic acid(s) into the host cell encoding the enzyme operably linked to a suitable promoter capable of transcription in the host cell, and optionally encoding the one or more enzyme(s) of a pathway for synthesizing Compound 1 from a carbon source; wherein the introducing step is prior to the culturing step. In some embodiments, the method further comprises separating Compound 2 from the host cell and/or the medium, wherein the separating step is subsequent, concurrent or partially concurrent with the culturing step.

The present invention further provides for an isolated compound 2 produced from the method of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
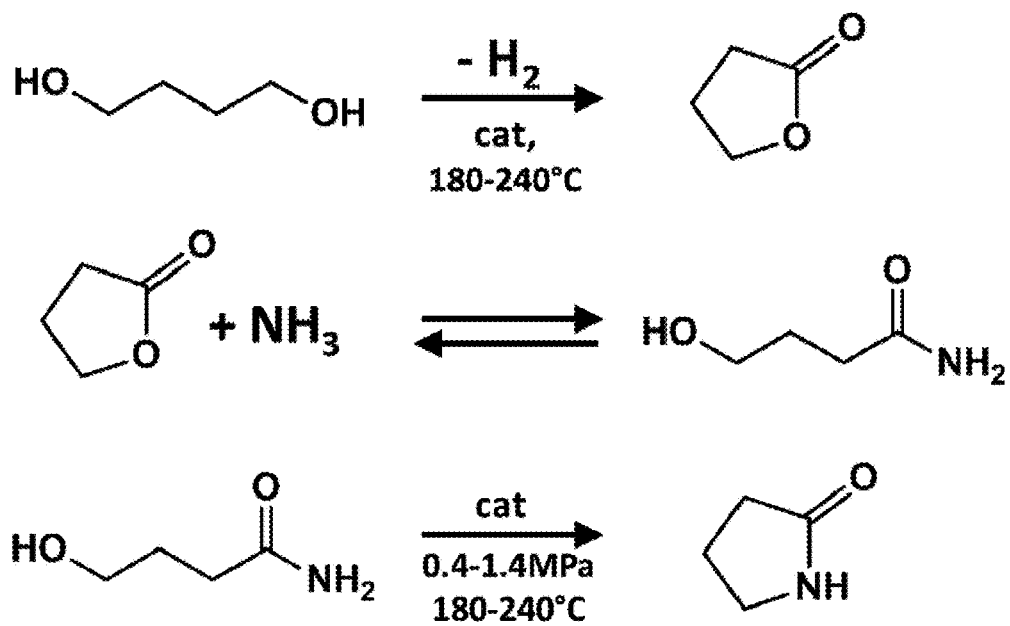
FIG. 1A. Route for production of 2-pyrrolidone: BASF petrochemical route for 2-pyrrolidone production. (B) Microbial 2-pyrrolidone biosynthetic route.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In order to more fully appreciate the invention the following definitions are provided.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The amino acid sequence of *Streptomyces aizunensis* ORF27 is:

In some embodiments, the host cell is capable of synthesizing Compound 1 or uptaking Compound 1 from the environment or culture. In some embodiments, the host cell further comprises one or more enzymes of a pathway for synthesizing Compound 1 from a carbon source. In some embodiments, the pathway for synthesizing Compound 1 from a carbon source is native to the host cell. In some embodiments, the pathway for synthesizing Compound 1 from a carbon source is heterologous to the host cell. In some embodiments, the carbon source is a carbon source the host cell in the wild-type form is capable of uptaking.

In some embodiments, the host cell comprises a first one or more nucleic acids encoding the 2-pyrrolidone synthase, or an enzymatically active fragment thereof, operably linked to a promoter capable of expressing the 2-pyrrolidone synthase, or an enzymatically active fragment thereof, in the host cell. In some embodiments, the host cell comprises a second one or more nucleic acids encoding one or more enzymes of a pathway for synthesizing Compound 1 from a carbon source, operably linked to a promoter capable of expressing the one or more enzymes of a pathway for synthesizing Compound 1 from a carbon source in the host cell. In some embodiments, the first and/or second nucleic acids are stably integrated into a chromosome of the host cell. In some embodiments, the first and/or second nucleic acids are capable of stable introduction into the host cell. In some embodiments, the first and/or second nucleic acids are vectors, or expression vectors. In some embodiments, the first and/or second nucleic acids are the same nucleic acid. In some embodiments, the first and/or second nucleic acids are separate nucleic acids.

```
                                                           (SEQ ID NO: 1)
  1 mrpmtakifa vdsvrpidef eqdalrvadv irergvclgd rvmlkagnsa syvcvlyalm 61 higasivlvd qqehkeetrr ialrtgvkvt fvddetpidq dadpihlyel mvatqnrppm 121 dsalsfdawg elsdglimwt sgstgspkgv vksggkflan lrrnahqvgh rpddvlmpll 181 pfahqyglsm vliawltrcs lviapyrrld ralrmardsg ttvidatpss yrsilglvtr 241 kpalrahlag trmfcvgaap ldaplvesyv qefglpllds ygstelnnia fatldnpvsc 301 gramegiglr ivdedgreva agqpgeievd tpdalegqia edgsiipapt gwqrtgdlgh 361 ldadgnlyvl grkfavhrmg ytlypelier kvaaegcptr ivplpdelrg sqlvffvedd 421 eqrdagywre rlcgllpafe qpnkvvvleq fpinrngkpd kkeltrmaae
```

The enzymatically active fragment is any polypeptide capable of catalyzing reaction (1). The enzymatically active fragment is an enzyme that has an amino acid sequence that is at least 70%, 75%, 80%, 85%, 90%, 95% or 99% identical to the amino acid sequence of SEQ ID NO:1. The enzymatically active fragment retains amino acids residues that are recognized as conserved for the enzyme. The enzymatically active fragment may have non-conserved amino acid residues replaced or found to be of a different amino acid, or amino acid(s) inserted or deleted, but which does not affect or has insignificant effect on the enzymatic activity of the enzymatically active fragment. The enzymatically active fragment may be found in nature or be an engineered mutant thereof. The enzymatically active fragment can comprise one or more of the following conserved amino acid sites/ residues: acyl-activating enzyme (AAE) consensus motif (residues 137, 140-145, 147-148), acyl-activating enzyme (AAE) consensus motif (residues 140, 257-258, 279-284, 357, 369, 372, 382, 458), AMP binding site (residues 140, 180-181, 227, 229-230, 233, 257-258, 279-284, 357, 369, 372, 379-382, 439), and CoA binding site (residues 180, 229-230, 233, 257, 379-381, 433, 439).

In some embodiments, the host cell lacks betaine-CoA ligase.

In some embodiments, n is an integer from 1 to 20. In some embodiments, n is an integer from 1 to 10. In some embodiments, n is an integer from 1 to 9. In some embodiments, n is an integer from 1 to 8. In some embodiments, n is an integer from 1 to 7. In some embodiments, n is an integer from 1 to 6. In some embodiments, n is an integer from 1 to 7. In some embodiments, n is an integer from 1 to 6. In some embodiments, n is an integer from 1 to 5. In some embodiments, n is an integer from 1 to 4. In some embodiments, n is an integer from 1 to 3. When n is 1, compound 2 is butyrolactam (2-pyrrolidone). When n is 2, compound 2 is valerolactam (2-piperidinone). When n is 3, compound 2 is caprolactam.

The host cell can be any eukaryotic cell, such as a yeast, or prokaryotic cell, such as a bacterium. In some embodiments, the host cell is yeast. Yeast host cells suitable for practice of the methods of the invention include, but are not limited to, *Yarrowia*, *Candida*, *Bebaromyces*, *Saccharomyces*, *Schizosaccharomyces* and *Pichia*, including engineered strains provided by the invention. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis, C. zeylenoides,* and *C. tropicalis.* In some embodiments the host cell is a bacterium, such as a Gram-positive or Gram-negative cell. Bacterial host cells suitable for practice of the methods of the invention include, but are not limited to, *Escherichia, Bacillus, Salmonella, Klebsiella, Enterobacter, Pseudomonas, Streptomyces, Cynechocystis, Cynechococcus, Sinorhizobium,* and *Caulobacter,* including engineered strains provided by the invention. In some embodiments, the 2-pyrrolidone synthase is heterologous to the cell.

References cited:

(1999). "The response to stationary-phase stress conditions in *Escherichia coli*: role and regulation of the glutamic acid decarboxylase system." *Mol Microbiol.* 32(6): 1198-1211.

(2002). "Biosynthesis and attachment of novel bacterial polyketide synthase starter units." *Nat Prod Rep* 19(1): 70-99.

Albrecht Ludwig Harreus, R. B., J.-O. Eichler, R. Feuerhake, C. Jakel, U. Mahn, R. Pinkos, R. Vogelsang (2011). 2-pyrrolidone. *Ullmann's Encyclopedia of Industrial Chemistry*, Wiley-VCH Verlag GmbH & Co. KGaA, Weinheim.

Amin, S. R., et al. (2013). "Prediction and experimental validation of enzyme substrate specificity in protein structures." *Proc Natl Acad Sci USA* 110(45): E4195-4202.

Baba, T., et al. (2006). "Construction of *Escherichia coli* K-12 in-frame, single-gene knockout mutants: the Keio collection." *Mol Syst Biol* 2.

Bachmann, B. O. (2010). "Biosynthesis: is it time to go retro?" *Nat Chem Biol* 6(6): 390-393.

Bachmann, B. O. N., TN, US), Mcalpine, James B. (Montréal, Calif.), Zazopoulos, Emmanuel (Montréal, Calif.), Farnet, Chris M. (2008). Polyene polyketides, processes for their production and their use as a pharmaceutical, Ecopia Biosciences Inc.

BASF (2015). "2-Pyrrolidone." Retrieved Mar. 5, 2015, from the webpage of: basf.ca/group/corporate/ca/en/brand/2_PYRROLIDONE.

Bernal, V., et al. (2008). "Role of betaine:CoA ligase (CaiC) in the activation of betaines and the transfer of coenzyme A in *Escherichia coli.*" *J Appl Microbiol* 105(1): 42-50.

Capitani G, D. B. D., Aurizi C, Gut H, Bossa F, Grütter M G. (2003). "Crystal structure and functional analysis of *Escherichia coli* glutamate decarboxylase." *EMBO J.* 22(16): 4027-4037.

Chaitan Khosla, J. D. K. (2003). "Metabolic engineering for drug discovery and development." *NATURE REVIEWS I DRUG DISCOVERY* 2: 1019.

Chang, A., et al. (2015). "BRENDA in 2015: exciting developments in its 25th year of existence." *Nucleic Acids Res* 43(Database issue): D439-446.

Dietrich, J. A., et al. (2010). "High-throughput metabolic engineering: advances in small-molecule screening and selection." *Annu Rev Biochem* 79: 563-590.

Dougherty, M. J. and F. H. Arnold (2009). "Directed evolution: new parts and optimized function." *Curr Opin Biotechnol* 20(4): 486-491.

Du, L. and L. Lou (2010). "PKS and NRPS release mechanisms." *Nat Prod Rep* 27(2): 255-278.

Du, L., et al. (2001). "Hybrid peptide-polyketide natural products: biosynthesis and prospects toward engineering novel molecules." *Metab Eng* 3(1): 78-95.

Dutta, S., et al. (2014). "Structure of a modular polyketide synthase." *Nature* 510(7506): 512-517.

Esvelt, K. M., et al. (2011). "A system for the continuous directed evolution of biomolecules." *Nature* 472(7344): 499-503.

Fluitt, A., et al. (2007). "Ribosome kinetics and aa-tRNA competition determine rate and fidelity of peptide synthesis." *Comput Biol Chem* 31(5-6): 335-346.

Galperin, M. Y. and E. V. Koonin (2012). "Divergence and convergence in enzyme evolution." *J Biol Chem* 287(1): 21-28.

James B. McAlpine, B. O. B., Mahmood Piraee, Steve Tremblay, Anne-Marie Alarco, Emmanuel Zazopoulos, and Chris M. Farnet (2005). "Microbial Genomics as a Guide to Drug Discovery and Structural Elucidation: ECO-02301, a Novel Antifungal Agent, as an Example." *J. Nat. Prod.* (68): 493-496.

Kalaitzis, J. A., et al. (2009). "In vitro biosynthesis of unnatural enterocin and wailupemycin polyketides." *J Nat Prod* 72(3): 469-472.

KAZUYO NISHIHARA, M. K., HIDEKI YANAGI, TAKASHI YURA (2000). "Overexpression of Trigger Factor Prevents Aggregation of Recombinant Proteins in *Escherichia coli.*" *Appl Environ Microbiol* 66(3): 884-889.

KAZUYO NISHIHARA, M. K., MASANARI KITAGAWA, HIDEKI YANAGI, AND TAKASHI YURA (1998). "Chaperone Coexpression Plasmids: Differential and Synergistic Roles of DnaK-DnaJ-GrpE and GroEL-GroES in Assisting Folding of an Allergen of Japanese Cedar Pollen, Cryj2, in *Escherichia coli.*" *Appl Environ Microbiol* 64(5): 1694-1699.

Khosla, C., et al. (2009). "Revisiting the modularity of modular polyketide synthases." *Curr Opin Chem Biol* 13(2): 135-143.

Kizer, L., et al. (2008). "Application of functional genomics to pathway optimization for increased isoprenoid production." *Appl Environ Microbiol* 74(10): 3229-3241.

Le Vo, T. D., et al. (2012). "Effects of glutamate decarboxylase and gamma-aminobutyric acid (GABA) transporter on the bioconversion of GABA in engineered *Escherichia coli.*" *Bioprocess Biosyst Eng* 35(4): 645-650.

Li, C., et al. (2009). "Analysis of the indanomycin biosynthetic gene cluster from *Streptomyces antibioticus* NRRL 8167." *Chembiochem* 10(6): 1064-1072.

Li, Y., et al. (2005). "Biosynthesis of the unique amino acid side chain of butirosin: possible protective-group chemistry in an acyl carrier protein-mediated pathway." *Chem Biol* 12(6): 665-675.

Llewellyn, N. M., et al. (2007). "Biosynthesis of butirosin: transfer and deprotection of the unique amino acid side chain." *Chem Biol* 14(4): 379-386.

Lohr, L. J. (1958). "The System of 2-pyrrolidone-water." *J. Phys. Chem.* 62 (9): 1150-1151.

Ma, D., et al. (2012). "Structure and mechanism of a glutamate-GABA antiporter." *Nature* 483(7391): 632-636.

Medema, M. H., et al. (2011). "Synthetic biology in *Streptomyces* bacteria." *Methods Enzymol* 497: 485-502.

Menzella, H. G., et al. (2005). "Combinatorial polyketide biosynthesis by de novo design and rearrangement of modular polyketide synthase genes." *Nat Biotechnol* 23(9): 1171-1176.

Moon, T. S. (2009). Retrobiosynthesis of D-Glucaric Acid in a Metabolically Engineered Strain of *Escherichia coli.*

Department of Chemical Engineering, MASSACHUSETTS INSTITUTE OF TECHNOLOGY. Doctor of Philosophy in Chemical Engineering: 181.

Ogasawara, Y., et al. (2004). "Cloning, sequencing, and functional analysis of the biosynthetic gene cluster of macrolactam antibiotic vicenistatin in *Streptomyces halstedii.*" *Chem Biol* 11(1): 79-86.

Päivi Pirilä, I. M., and Jouni Pursiainen (1999). "structure of 2-pyrrolidone monohydrate." *Z. Naturforsch.* 54b: 1598-1601.

Park, S. J., et al. (2013). "Synthesis of nylon 4 from gamma-aminobutyrate (GABA) produced by recombinant *Escherichia coli.*" *Bioprocess Biosyst Eng* 36(7): 885-892.

Pennacchietti, E., et al. (2009). "Mutation of His465 alters the pH-dependent spectroscopic properties of *Escherichia coli* glutamate decarboxylase and broadens the range of its activity toward more alkaline pH." *J Biol Chem* 284(46): 31587-31596.

Proshkin, S., et al. (2010). "Cooperation between translating ribosomes and RNA polymerase in transcription elongation." *Science* 328(5977): 504-508.

Sakuda, S., et al. (1996). "Novel linear polyene antibiotics: linearmycins." *Journal of the Chemical Society, Perkin Transactions* 1(18): 2315.

Shi, F., et al. (2013). "Enhancement of gamma-aminobutyric acid production in recombinant *Corynebacterium glutamicum* by co-expressing two glutamate decarboxylase genes from *Lactobacillus brevis.*" *J Ind Microbiol Biotechnol* 40(11): 1285-1296.

Shinohara, Y., et al. (2011). "A natural protecting group strategy to carry an amino acid starter unit in the biosynthesis of macrolactam polyketide antibiotics." *J Am Chem Soc* 133(45): 18134-18137.

Shiue, E. and K. L. Prather (2014). "Improving D-glucaric acid production from myo-inositol in *E. coli* by increasing MIOX stability and myo-inositol transport." *Metab Eng* 22: 22-31.

Siller, E., et al. (2010). "Slowing bacterial translation speed enhances eukaryotic protein folding efficiency." *J Mol Biol* 396(5): 1310-1318.

Simunovic, V., et al. (2006). "Myxovirescin A biosynthesis is directed by hybrid polyketide synthases/nonribosomal peptide synthetase, 3-hydroxy-3-methylglutaryl-CoA synthases, and trans-acting acyltransferases." *Chembiochem* 7(8): 1206-1220.

Stavila, E. and K. Loos (2013). "Synthesis of lactams using enzyme-catalyzed aminolysis." *Tetrahedron Letters* 54(5): 370-372.

Studier, F. W. (2005). "Protein production by auto-induction in high-density shaking cultures." *Protein Expr Purif* 41(1): 207-234.

T. Werpy, G. P. (2004). "Top Value Added chemicals from Biomass." Volume I—results of screening for potential candidates from sugars and synthesis gas.

T. Ruusala, D. A., M. Ehrenberg and C. G. Kurland (1984). "Hyper-accurate ribososomes inhibit growth." *The EMBO Journal* 3(11): 2575-2580.

Takahashi, C., et al. (2012). "Robust production of gamma-amino butyric acid using recombinant *Corynebacterium glutamicum* expressing glutamate decarboxylase from *Escherichia coli.*" *Enzyme Microb Technol* 51(3): 171-176.

Tran, L., et al. (2010). "Insights into protein-protein and enzyme-substrate interactions in modular polyketide synthases." *Chem Biol* 17(7): 705-716.

Weissman, K. J. and R. Muller (2008). "Protein-protein interactions in multienzyme megasynthetases." *Chembiochem* 9(6): 826-848.

Wenjun Zhang, M. L. B., Daniel Kahne, and Christopher T. Walsh (2010). "A Three Enzyme Pathway for 2-Amino-3-hydroxycyclopent-2-enone Formation and Incorporation in Natural Product Biosynthesis." *J. AM. CHEM. SOC.* 132: 6402-6411.

Wong, F. T., et al. (2010). "Protein-protein recognition between acyltransferases and acyl carrier proteins in multimodular polyketide synthases." *Biochemistry* 49(1): 95-102.

Yadav, G., et al. (2009). "Towards prediction of metabolic products of polyketide synthases: an in silico analysis." *PLoS Comput Biol* 5(4): e1000351.

Zazopoulos, E., et al. (2003). "A genomics-guided approach for discovering and expressing cryptic metabolic pathways." *Nat Biotechnol* 21(2): 187-190.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Metabolic Engineering of *Escherichia coli* for the Biosynthesis of 2-Pyrrolidone 2-Pyrrolidone is a "top value-added chemical" from biomass with myriad applications as a solvent, polymer precursor and active pharmaceutical intermediate. A novel 2-pyrrolidone synthase from *Streptomyces aizunensis* ORF27 was identified by retro-biosynthetic analysis of polyketide natural products. ORF27 catalyzes the ATP dependent ring closing of γ-aminobutyrate to form 2-pyrrolidone. Although ORF27 had the tendency to aggregate and lose activity, expression at 25° C. and fusing to the maltose binding protein increased its activity in vivo. Recombinant *Escherichia coli* was metabolically engineered for the production of 2-pyrrolidone from glutamate by expressing both the genes encoding GadB, a glutamate decarboxylase, and ORF27. *E. coli*'s native CaiC, a betaine-CoA ligase, was also discovered to be able to catalyze 2-pyrrolidone formation from GABA, representing an unintended crosstalk during high flux microbial biosynthesis. A GadB mutant lacking $His^{465}$ and $Thr^{466}$, GadB_ΔHT, has higher activity at intracellular pH than the native GadB, incorporation of which improved the efficiency of one-pot 2-pyrrolidone biosynthesis in vivo. When the recombinant *E. coli* strain expressing the *E. coli* GadB_ΔHT mutant, plus the *Streptomyces aizunensis* ORF27 MBP fusion was cultured in ZYM-5052 medium containing 9 g/L of L-glutamate, 1.1 g/L of 2-pyrrolidone was produced by converting 7.7 g/L of L-glutamate within 31 h, achieving 25% conversion.

Figure 1B:
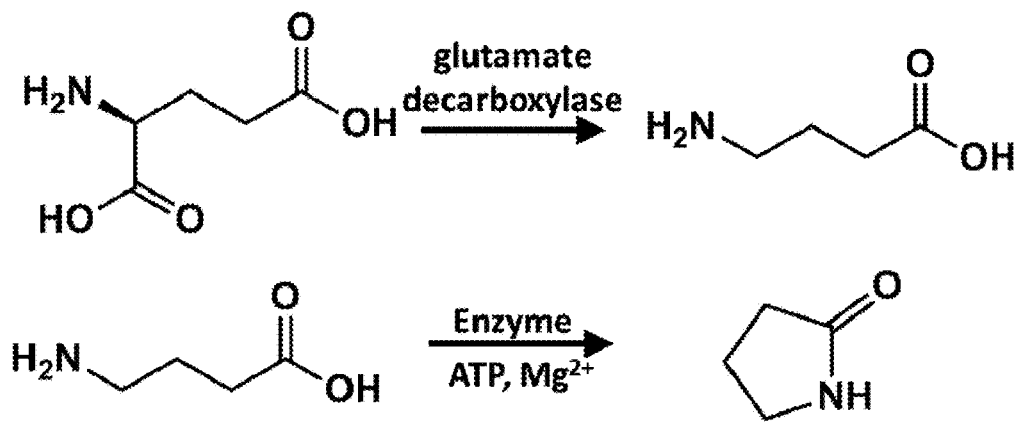
FIG. 1B. Route for production of 2-pyrrolidone: Microbial 2-pyrrolidone biosynthetic route.

We propose a two enzymatic step microbial process for 2-pyrrolidone biosynthesis from glutamate: 1) decarboxylation of glutamate to form γ-aminobutyrate (GABA); 2) enzymatic ring closing of GABA into 2-pyrrolidone (FIG. 1B).

While the first enzymatic step is known (Le Vo, Kim et al. 2012, Ma, Lu et al. 2012, Takahashi, Shirakawa et al. 2012, Park, Kim et al. 2013, Shi, Jiang et al. 2013), the second step has not been demonstrated under mild fermentation conditions (Stavila and Loos 2013). Retrobiosynthetic analysis, a product-targeted design of biological pathways, has previously been applied to uncover the necessary enzymatic transformation of substrates (Moon 2009, Bachmann 2010). However, even the relatively comprehensive enzyme databases, such as BRENDA, cannot cover unprecedented enzymatic reactions on specific substrates, in this case 2-pyrrolidone synthase (Chang, Schomburg et al. 2015). Poor prediction of enzyme substrate activities via bioinformatics or computation makes it difficult to identify the exact gene candidate from a huge list of protein homologs (Amin, Erdin et al. 2013). Therefore, significant trial and error process is usually involved during enzyme discovery.

We employed a targeted strategy to identify appropriate enzyme candidates for the GABA activation step by conducting retro-biosynthetic analysis of polyketides. Type I polyketide synthases are mega-synthases whose enzymatic domain organization predictably correlate with their natural product's chemical structure—usually referred to as the colinearity rule (Du, Sanchez et al. 2001, Menzella, Reid et al. 2005, Weissman and Muller 2008, Khosla, Kapur et al. 2009, Li, Roege et al. 2009, Yadav, Gokhale et al. 2009, Du and Lou 2010, Tran, Broadhurst et al. 2010, Wong, Chen et al. 2010, Dutta, Whicher et al. 2014). While PKS genes are responsible for biosynthesis of the characteristic polyketide aglycone backbone, auxiliary enzymes are involved in starter unit activation and/or post aglycone modification (2002, Ogasawara, Katayama et al. 2004, Li, Llewellyn et al. 2005, Simunovic, Zapp et al. 2006, Llewellyn, Li et al. 2007, Kalaitzis, Cheng et al. 2009, Shinohara, Kudo et al. 2011).

The close positioning of PKS genes with auxiliary enzymes in the same gene cluster makes it easy to pinpoint the substrate these auxiliary enzymes act on. Here we report the discovery in *Streptomyces aizunensis* of ORF27, an auxiliary enzyme in the linearmycin A biosynthetic cluster that performs the GABA activation step to form 2-pyrrolidone under mild fermentation conditions. Coupling this 2-pyrrolidone synthase with glutamate decarboxylase, which forms GABA from glutamate, we achieved the first demonstration of the full 2-pyrrolidone biosynthetic pathway in *E. coli*.

Therefore, we propose a two enzymatic step microbial process towards 2-pyrrolidone biosynthesis from glutamate: 1) decarboxylation of glutamate to form γ-aminobutyrate (GABA); 2) activation of GABA's acid group, allowing self-lactamization to form 2-pyrrolidone (FIG. 1B).

While the first enzymatic step is known, the second step has not been demonstrated at mild fermentation conditions. The enzyme database, such as Brenda-enzymes suffers from incomplete coverage of unreported or even reported enzymatic reactions. Poor prediction of enzyme substrate via bioinformatics or computation made it hard to identify the exact gene candidate from a huge list of protein homologs. Therefore, significant trial and error is usually involved during enzyme discovery. We employed a targeted strategy to identify appropriate enzyme candidates for the GABA activation step by conducting retro-biosynthetic analysis of polyketides.

Type I polyketide synthases are mega-synthases whose enzymatic domain organization predictably correlate with their natural product's chemical structure—usually referred to as the colinearity rule. While PKS genes are responsible for biosynthesis of the characteristic polyketide aglycone backbone, auxiliary enzymes are involved in starter unit activation and/or post aglycone modification. The close positioning of PKS genes with auxiliary enzymes in the same gene cluster makes it easy to pinpoint the substrate these auxiliary enzyme act on. Here we report the discovery in *Streptomyces aizunensis* of ORF27, an auxiliary enzyme in Eco-02301 biosynthetic cluster, that perform the GABA activation step under mild fermentation conditions. Coupling this 2-pyrrolidone synthase with glutamate decarboxylase that forms GABA, we achieved the first demonstration of the full 2-pyrrolidone biosynthetic pathway in *E. coli*.

2. Materials and Methods 2.1. Retro-Biosynthetic Analysis of PKS Natural Products Literature review combined with PKS databases, such as NRPS-PKS (the webpage of: nii.res.in/nrps-pks.html), MAPSI (http://gate.smallsoft.co.kr:8008/pks/mapsidb/), NORINE (http://bioinfo.lifl.fr/norine/), DoBISCUIT (the webpage of: bio.nite.go.jp/pks/), PKMiner (http://pks.kaist-.ac.kr/pkminer/) and ClusterMine360 (the webpage of: clustermine360.ca/), were explored to identify polyketides with both positively charged, amine-containing starter units and gene cluster sequence information. Retrobiosynthetic analysis of polyketide natural products was performed to predict starter units that are GABA or its close analogs. Sequence information was further analyzed for auxiliary enzyme ORF annotation and function prediction. The hypothesized reaction candidates were reverse transcribed using the optimized *E. coli* codon usage using DNA 2.0's algorithm and synthesized and prepared to be heterologously expressed in *E. coli* for characterization.

2.2. Bacterial Strains, Plasmids and Chemicals

*E. coli* strain DH10B [F-mcrA Δ(mrr-hsdRMS-mcrBC) φ80dlacZΔM15 ΔlacX74 recA1 endA1 araD139 Δ(ara, leu) 7697 galU galK λ-rpsL (Strr) nupG] was used for all molecular biology manipulations. DH10B and BL21 Star (DE3) [F-ompT hsdSB (rB-mB-) gal dcm rne131 (DE3)] were used as hosts for production of 2-pyrrolidone. Competent cells of both strains were purchased from Invitrogen Corporation (Carlsbad, Calif.). All the strains, plasmids, and oligonucleotides utilized in this study are listed in Tables 1-3. Cultures were propagated in Luria-Bertani (LB) medium. LB (Miller) medium was prepared from dehydrated powder according to the manufacturer's instructions (BD Biosciences, San Jose, Calif.). Nickel nitrilotriacetic acid agarose (Ni-NTA) resin and SDS-PAGE gels were purchased from Qiagen and Biorad, respectively. Protein samples were concentrated using 10 KDa MMCO Amicon Ultra filters (Millipore). DNA and protein concentrations were determined using a Nanodrop 1000 spectrophotometer (Thermo Scientific). For high-density shake flask cultures, Studier's autoinduction ZYM-5052 medium was prepared according to the published protocol.

Chloramphenicol (25 µg/mL), kanamycin (20 µg/ml) and ampicillin (100 µg/ml) were added where desired to provide selective pressure for plasmid maintenance. During 2-pyrrolidone production, one-quarter of the antibiotic concentration was used: chloramphenicol (6.25 µg/mL), kanamycin (5 µg/ml) and ampicillin (25 µg/ml). 2-Pyrrolidone, glutamic acid, GABA, and ATP were purchased from Sigma-Aldrich (St. Louis, Mich.).

TABLE 1

Strains used.

| Name Strains | Relevant genotype | References |
|---|---|---|
| DH10B | F– mcrA Δ(mrr-hsdRMS-mcrBC) φ80lacZΔM15 ΔlacX74 recA1 endA1 araD139 Δ(ara, leu)7697 galU galK λ–rpsL nupG | Life Technologies (Carlsbad, CA) |
| BL21 Star (DE3) | F– ompT hsdSB (rB– mB–) gal dcm rne131 (DE3) | Life Technologies (Carlsbad, CA) |
| JW2637-4 | F–, Δ(araD-araB)567, ΔlacZ4787(::rrnB-3), λ–, ΔgabT743::kan, rph-1, Δ(rhaD-rhaB)568, hsdR514 | CGSC #11775 |
| JW0036-1 | F–, Δ(araD-araB)567, ΔlacZ4787(::rrnB-3), λ–, ΔCaiC750::kan, rph-1, Δ(rhaD-rhaB)568, hsdR514 | CGSC #8352 |
| W3110 | F– lambda– IN(rrnD-rrnE)1 rph-1 | CGSC #4474 |
| CH184 | F– lambda– IN(rrnD-rrnE)1 rph-1, rpsL_C256A_C272A | T. Ruusala et al. (1984) |

| Strains | plasmids | Host |
|---|---|---|
| JZ-298 | pBbS2C-ORF27 | JW2637-4 |
| JZ-172 | pBbE2C-RFP | JW2637-4 |
| JZ-393 | pBbE2C-RFP | JW0036-1 |
| JZ-171 | pBbE2C-ORF27 | JW2637-4 |
| JZ-297 | pBbE2C-ORF36 | JW2637-4 |
| JZ-299 | pBbE2C-MBP-ORF27 | JW2637-4 |
| JZ-316 | pBbE2C-MBP-ORF27 | W3110 |
| JZ-317 | pBbE2C-MBP-ORF27 | CH184 |
| JZ-370 | pBbE2C-CaiC | JW2637-4 |
| JZ-336 | pBbE2C-MBP-ORF27 + pBbA5a-GadB WT | BL21 Star (DE3) |
| JZ-338 | pBbE2C-MBP-ORF27 + pBbA5a-GadB_ΔHT | BL21 Star (DE3) |
| JZ-339 | pBbE2C-MBP-ORF27 + pBbA5a-GadB_Δ1-14 | BL21 Star (DE3) |
| JZ-340 | pBbE2C-MBP-ORF27 + pBbA5a-GadB_Δ1-14, ΔHT | BL21 Star (DE3) |
| JZ-342 | pET28a-MBP-ORF27 + pBbA7a-GadB WT | BL21 Star (DE3) |
| JZ-344 | pET28a-MBP-ORF27 + pBbA7a-GadB_ΔHT | BL21 Star (DE3) |
| JZ-345 | pET28a-MBP-ORF27 + pBbA7a-GadB_Δ1-14 | BL21 Star (DE3) |
| JZ-346 | pET28a-MBP-ORF27 + pBbA7a-GadB_Δ1-14, ΔHT | BL21 Star (DE3) |
| JZ-348 | pBbE2C-MBP-ORF27 + pBbA7a-GadB WT | BL21 Star (DE3) |
| JZ-350 | pBbE2C-MBP-ORF27 + pBbA7a-GadB_ΔHT | BL21 Star (DE3) |
| JZ-351 | pBbE2C-MBP-ORF27 + pBbA7a-GadB_Δ1-14 | BL21 Star (DE3) |
| JZ-352 | pBbE2C-MBP-ORF27 + pBbA7a-GadB_Δ1-14, ΔHT | BL21 Star (DE3) |
| JZ-376 | takara KJE7(Cm) + pET28a-MBP-ORF27 + pBbA7a-GadB_ΔHT | BL21 Star (DE3) |
| JZ-377 | takara Tf16(Cm) + pET28a-MBP-ORF27 + pBbA7a-GadB_ΔHT | BL21 Star (DE3) |
| JZ-378 | takara pGro7 (Cm) + pET28a-MBP-ORF27 + pBbA7a-GadB_ΔHT | BL21 Star (DE3) |
| JZ-379 | takara Tf2 (Cm) + pET28a-MBP-ORF27 + pBbA7a-GadB_ΔHT | BL21 Star (DE3) |
| JZ-380 | takara KJE8 (Cm) + pET28a-MBP-ORF27 + pBbA7a-GadB_ΔHT | BL21 Star (DE3) |
| JZ-386 | pET28b-N-CaiC + pBbA7a-GadB_ΔHT | BL21 Star (DE3) |

TABLE 2

Plasmids used.

| Plasmids | | |
|---|---|---|
| pDNA2.0-ORF27 | pUC ori, Kan$^R$, ORF27 with Biobrick overhang | DNA 2.0 (Menlo Park, CA) |
| pDNA2.0-ORF36 | pUC ori, Kan$^R$, ORF36 with Biobrick overhang | DNA 2.0 (Menlo Park, CA) |
| pBbE2C-RFP | ColE ori, Cm$^R$, tetR, RFP | TS. Lee (2011) |
| pBbE2C-ORF27 | ColE ori, Cm$^R$, tetR, ORF27 | This study |
| pBbE2C-CaiC | ColE ori, Cm$^R$, tetR, CaiC | This study |
| pBbE2C-ORF36 | ColE ori, Cm$^R$, tetR, ORF36 | This study |
| pBbS2C-RFP | SC101 ori, CmR, tetR, RFP | TS. Lee (2011) |

TABLE 2-continued

Plasmids used.

| Plasmids | | |
|---|---|---|
| pBbS2C-ORF27 | SC101 ori, Cm$^R$, tetR, ORF27 | This study |
| pET28b | pBR322 ori, Kan$^R$, lacI, MCS after P$_{T7}$ | EMD Millipore (Billerica, MA) |
| pET28b-N-ORF27 | pET28b with ORF27 inserted into NdeI and XhoI | This study |
| pET28b-N-CaiC | pET28b with CaiC inserted into NdeI and XhoI | This study |
| pET28b-C-ORF27 | pET28b with ORF27 inserted into NcoI and XhoI | This study |
| pET28a-MBP | pBR322 ori, Kan$^R$, lacI, MCS after MBP fusion driven by P$_{T7}$ | EMD Millipore (Billerica, MA) |
| pET28a-MBP-ORF27 | pET28a-MBP with ORF27 inserted into NdeI and XhoI | This study |
| pBbE2C-MBP-ORF27 | ColE ori, Cm$^R$, tetR, MBP-ORF27 | This study |
| pBbA5a-GadB | p15A ori, AmpR, Placuv5, GadB | This study |
| pBbA5a-GadB_ΔHT | p15A ori, AmpR, Placuv5, GadB_ΔHT | This study |
| pBbA5a-GadB_Δ1-14 | p15A ori, AmpR, Placuv5, GadB_Δ1-14 | This study |
| pBbA5a-GadB_Δ1-14_ΔHT | p15A ori, AmpR, Placuv5, GadB_Δ1-14, ΔHT | This study |
| pBbA7a-RFP | p15A ori, AmpR, PT7, RFP | T.S. Lee (2011) |
| pBbA7a-GadB | p15A ori, Amp$^R$, P$_{T7}$, GadB | This study |
| pBbA7a-GadB_ΔHT | p15A ori, Amp$^R$, P$_{T7}$, GadB_ΔHT | This study |
| pBbA7a-GadB_Δ1-14 | p15A ori, Amp$^R$, P$_{T7}$, GadB_Δ1-14 | This study |
| pBbA7a-GadB_Δ1-14_ΔHT | p15A ori, Amp$^R$, P$_{T7}$, GadB_Δ1-14_ΔHT | This study |
| pG-Tf2 | P$_{P2tl}$, groES-groEL-tig, Cm$^R$ | Clontech Laboratories, Inc. (Mountain View, CA) |
| pKJE7 | P$_{araB}$, dnaK-dnaJ-grpE, Cm$^R$ | Clontech Laboratories, Inc. (Mountain View, CA) |
| pTf16 | P$_{P2tl}$, tig, Cm$^R$ | Clontech Laboratories, Inc. (Mountain View, CA) |
| pGro7 | P$_{araB}$, groES-groEL, Cm$^R$ | Clontech Laboratories, Inc. (Mountain View, CA) |
| pKJE8 | P$_{araB}$, dnaK-dnaJ-grpE; P$_{P2tl}$, groES-groEL, Cm$^R$ | Clontech Laboratories, Inc. (Mountain View, CA) |

TABLE 3

Oligonucleotides used.

| Oligonucleotides | 5'→3' Sequence, restriction site underlied, synthesized by Integrated DNA Technologies, Inc (Coralville, IA) | Target Gene |
|---|---|---|
| JZ_27_C6xHis_f | GCGCGccatgg gc ATGCGCCCAATGAC CGCTAAAATCTTCG (SEQ ID NO: 2) | C-6xHis-ORF27 |
| JZ_27_C6xHis_r | GCGCGctcgagTTCTGC CGCCATACGGGTCAGC (SEQ ID NO: 3) | C-6xHis-ORF27 |
| JZ_MBP-ORF27_f | GCGCGgaattcaaaaga tcttttaagaaggagat atacatatggcagcag ccatcatca (SEQ ID NO: 4) | MBP-ORF27 |
| JZ_MBP-ORF27_r | GCGCGctcgagtttgga tccTCATTCTGCCGCCA TACGGG (SEQ ID NO: 5) | MBP-ORF27 |
| JZ_GadB_f | gcgcgCATATGgataaga agcaagtaacg (SEQ ID NO: 6) | GadB, GadB_ΔHT, GadB_H465A |
| JZ_GadB_r | gcgcgGGATCCTTAtcag gtatgtttaaagctgtt (SEQ ID NO: 7) | GadB, GadB_Δ1-14 |

TABLE 3-continued

Oligonucleotides used.

| Oligonucleotides | 5'→3' Sequence, restriction site underlied, synthesized by Integrated DNA Technologies, Inc (Coralville, IA) | Target Gene |
|---|---|---|
| JZ_GadB1-14_f | gcgcgCATATGGGTT CACGTTTTGGTGCGA (SEQ ID NO: 8) | GadB_Δ1-14, GadB_Δ1-14_AHTGadB_Δ1-14_H465A |
| JZ_GadB_H465A_r | gcgcgGGATCCTTAtcag gtaGCtttaaagctgttc tgttggg (SEQ ID NO: 9) | GadB_Δ1-14_H465A GadB_H465A |
| JZ_GadBΔHT_r | gcgcgGGATCCTTAtcatt taaagctgttctgttggg (SEQ ID NO: 10) | GadB_Δ1-14_ΔHT GadB_ΔHT |
| JZ_CaiC_f | GCGCgaattcaaaagatctt ttaagaaggagatatacatA TGGATAGAGGTGCAATGGAT (SEQ ID NO: 11) | CaiC |
| JZ_CaiC_r | GCGCG ctcgagtttggatccTTATT TCAGATTCTTTCTAATTATT TTCCCC (SEQ ID NO: 12) | CaiC |

2.3. Plasmid Construction

All molecular biology manipulations were performed according to standard practices (Sambrook and Russell, 2001). Genes encoding ORF27 (GenBank: AAX98201.1) and ORF36 (GenBank: AAX98210.1) were recoded using *E. coli* codon usage with biobrick overhangs 5'-gaattcaaa AGATCTAGGAGGCAT-3' (SEQ ID NO:13) on the 5' end and 5'-TAAGGATCCAAACTCGAG-3' (SEQ ID NO:14) on the 3' end. DNA 2.0 (Menlo Park, Calif.) cloned the genes into plasmid vectors creating pDNA2.0-ORF27 and pDNA2.0-ORF36, respectively. The genes encoding wild-type GadB and the variant GadB_ΔHT, were amplified from *E. coli* MG1655 genomic DNA using the primers specified. GadB_ΔHT lacks histidine 465 and threonine 466 of *E. coli* GadB. The construction of each plasmid is described in Table 4.

TABLE 4

Plasmid construction.

| Constructed Plasmid | Backbone Source (restriction site) | Gene Source (direct digestion or PCR) | PCR primers |
|---|---|---|---|
| pBbE2C-ORF27 | pBbE2C-RFP (BglII, XhoI) | pDNA2.0-ORF27 (BglII, XhoI) | N/A |
| pBbE2C-ORF36 | pBbE2C-RFP (BglII, XhoI) | pDNA2.0-ORF36 (BglII, XhoI) | N/A |
| pBbS2C-ORF27 | pBbS2C-RFP (BglII, XhoI) | pDNA2.0-ORF27 (BglII, XhoI) | N/A |
| pET28b-N-ORF27 | pET28b (NdeI, XhoI) | pDNA2.0-ORF27 (NdeI, XhoI) | N/A |
| pET28b-N-CaiC | pET28b (NdeI, XhoI) | pBbE2C-CaiC (NdeI, XhoI) | N/A |
| pET28b-C-ORF27 | pET28b (NcoI, XhoI) | pDNA2.0-ORF27 PCR | JZ_27_C6xHis_f, JZ_27_C6xHis_r |
| pBbE2C-ORF27 | pBbE2C-RFP (BglII, XhoI) | pDNA2.0-ORF27 (BglII, XhoI) | N/A |
| pBbE2C-CaiC | pBbE2C-RFP (EcoRI, XhoI) | *E. coli* MG1655 gDNA PCR | JZ_CaiC_f, JZ_CaiC_r |
| pET28a-MBP-ORF27 | pET28a-MBP (NdeI, XhoI) | pDNA2.0-ORF27 (NdeI, XhoI) | N/A |
| pBbE2C-MBP-ORF27 | pBbE2C-RFP (BglII, XhoI) | pET28a-MBP-ORF27 PCR | JZ_MBP-ORF27_f, JZ_MBP-ORF27_r |
| pBbA5a-GadB | pBbA5a-RFP (NdeI, BamHI) | *E. coli* MG1655 gDNA PCR | JZ_GadB_f, JZ_GadB_r |
| pBbA5a-GadB_ΔHT | pBbA5a-RFP (NdeI, BamHI) | *E. coli* MG1655 gDNA PCR | JZ_GadB_f, JZ_GadB_ΔHT_r |
| pBbA5a-GadB_Δ1-14 | pBbA5a-RFP (NdeI, BamHI) | *E. coli* MG1655 gDNA PCR | JZ_GadBΔ1-14_f, JZ_GadB_r |
| pBbA5a-GadB_Δ1-14, ΔHT | pBbA5a-RFP (NdeI, BamHI) | *E. coli* MG1655 gDNA PCR | JZ_GadBΔ1-14_f, JZ_GadB_ΔHT_r |
| pBbA7a-GadB | pBbA7a-RFP (NdeI, BamHI) | pBbA5a-GadB (NdeI, BamHI) | N/A |
| pBbA7a-GadB_ΔHT | pBbA7a-RFP (NdeI, BamHI) | pBbA5a-GadB_ΔHT (NdeI, BamHI) | N/A |
| pBbA7a-GadB_Δ1-14 | pBbA7a-RFP (NdeI, BamHI) | pBbA5a-GadB_Δ1-14 (NdeI, BamHI) | N/A |

TABLE 4-continued

Plasmid construction.

| Constructed Plasmid | Backbone Source (restriction site) | Gene Source (direct digestion or PCR) | PCR primers |
|---|---|---|---|
| pBbA7a-GadB_Δ1-14_ΔHT | pBbA7a-RFP (NdeI, BamHI) | pBbA5a-GadB_Δ1-14, ΔHT(NdeI, BamHI) | N/A |

2.4. ORF27 Protein Expression and Purification

For expression and purification of ORF27, the ORF27 gene was cloned into pET28b and the resulting plasmid, pET28b-N-ORF27, was transformed into *E. coli* BL21 Star (DE3) for N-terminal 6×His ORF27 overexpression. The overnight culture was inoculated (1:100 v/v) into 1 L LB medium containing 5 μg/ml kanamycin. The culture was grown at 37° C. until the O.D. reached 0.6 and cooled on ice for 20 min. 0.5 mM IPTG was added to induce N-6×His ORF27overexpression for 16 h at 18° C. The cells were harvested by centrifugation (8000×g, 6 min, 4° C.), resuspended in 30 mL of lysis buffer (50 mM HEPES, pH 8.0, 0.5 M NaCl, and 10 mM imidazole), and lysed by sonication on ice. Cellular debris was removed by centrifugation (20,000× g, 30 min, 4° C.). Ni-NTA agarose resin was added to the supernatant (1 mL/L of culture), and the solution was rocked at 4° C. for 1 h. The protein resin mixture was loaded onto a gravity flow column, and proteins were washed with washing buffer (50 mM HEPES, pH 8.0, 0.5 M NaCl, and 20 mM imidazole) and eluted with elution buffer (50 mM HEPES, pH 8.0, 0.5 M NaCl, and 250 mM imidazole). Purified proteins (60 mg from 1 L culture) were concentrated to 280 mg/mL and buffer exchanged into storage buffer (50 mM HEPES, pH 8.0, 8% glycerol). The final proteins were aliquoted and flash frozen in liquid nitrogen and stored at −80° C. C-terminal 6×His ORF27 (65 mg/L LB culture) was produced using BL21 Star (DE3) transformed with pET28b-C-ORF27, purified by Ni-NTA agarose resin and stocked at 220 mg/mL in storage buffer (50 mM HEPES, pH 8.0, 8% glycerol).

2.5. 2-Pyrrolidone, GABA and Glutamate Liquid Chromatography-Mass Spectrometry Product Assays 2.5.1 Liquid Chromatography Method for 2-pyrrolidone, GABA and Glutamate Separation Liquid chromatography (LC) separation of 2-pyrrolidone was conducted at 55° C. with an Inertsil ODS-3 reverse-phase C18 column (250 mm length, 2.1 mm internal diameter, 3 μM particle size; GL Sciences) using a 1100 series high-performance LC system (Agilent Technologies). The mobile phase was composed of 0.1% formic acid in $H_2O$ (solvent A) and 0.1% formic acid in MeOH (solvent B). Butyrolactam was separated with the following gradient: 40% to 60% B for 4.5 min, 60% to 100% B for 1.5 min, 100% to 40% B for 0.5 min, held at 10% B for 8.5 min. A flow rate of 0.18 mL/min was used throughout.

2.5.2 Mass Spectrometry Analysis of 2-pyrrolidone, GABA and Glutamate 2.5.2.1 Time-of-Flight Mass Spectrometry Method for 2-pyrrolidone, GABA Dimer Accurate Mass Monitoring The LC system was coupled to an Agilent Technologies 6210 electrospray time-of-flight (TOF) mass spectrometer. Nitrogen gas was used as both the nebulizing and drying gas to facilitate the production of gas-phase ions. The drying and nebulizing gases were set to 11 L/min and 25 psig, respectively, and a drying gas temperature of 320° C. was used throughout. ESI was conducted in the positive-ion mode with a capillary voltage of 3.5 kV. Mass measurements were carried out in the TOF-Scan monitoring mode for the detection of [M+H]+ ions (2-pyrrolidone, m/z=86.0600; GABA dimer, m/z=189.1234). The instrument was tuned for a range of m/z 70 to 300. Data acquisition and processing were performed using Chemstation (Agilent Technologies).

2.5.2.2 Selected Ion Monitoring Mass Spectrometry Method for 2-pyrrolidone, GABA, Glutamate Quantification The LC system was coupled to an Agilent Technologies LC-MSD SL electrospray ionization mass (ESI MS) spectrometer. Nitrogen gas was used as both the nebulizing and drying gas to facilitate the production of gas-phase ions. The drying and nebulizing gases were set to 10 L/min and 20 psig, respectively, and a drying gas temperature of 300° C. was used throughout. ESI was conducted in the positive-ion mode with a capillary voltage of 4 kV. Mass measurements were carried out in the selected ion monitoring (SIM) mode (2-pyrrolidone, m/z 86; GABA, m/z 104; glutamate, m/z 148) for the detection of [M+H]+ ions. Data acquisition and processing were performed using Agilent Chemstation software (Agilent Technologies).

2.6. In Vitro Product Assay for ORF27

To confirm the minimal system for ORF27-catalyzed 2-pyrrolidone formation, a reaction mixture containing 5 μM of ORF27, 1 mM GABA substrates, 1 mM ATP and 1 mM $Mg(Cl)_2$ in 100 mM HEPES (pH 7.5) and incubated at 25° C. for 30 min. The reactions were quenched by addition of methanol to a final concentration of 50% (v/v), and the supernatant filtered through 10 K Amicon Ultra-0.5 mL Centrifugal Filters (Millipore). The filtered solution was analyzed using the LC-MS-TOF method described above. Control reactions were carried out without enzyme, without ATP, or without $MgCl_2$ (supplying additional 0.2 mM EDTA).

2.7. 2-Pyrrolidone Production Titer Determination

600 μL of culture was cooled on ice and centrifuged at 18,000×g for 5 min at 4° C. 250 μL of the supernatant was mixed with 250 μL methanol to a final concentration of 50% (v/v), and the mixed solution filtered through 10 K Amicon Ultra-0.5 mL Centrifugal Filters (Millipore) by centrifuging at 20,000×g for 15 min. The filtered solution was diluted into the respective linear range of detection for 2-pyrrolidone and analyzed by LC-MS-TOF.

2.8. Culture Conditions 2.8.1 Inducible 2-pyrrolidone Production from GABA

*E. coli* strains (JZ-298, JZ-171, JZ-297, JZ-299, JZ-316, JZ-317, JZ-370, JZ-393) carrying the proposed GABA activating enzyme expression plasmids (ORF27, MBP-ORF27 or CaiC) were inoculated into 25-mL LB medium with chloramphenicol (25 μg/mL) and grown at 37° C. *E. coli* expressing RFP was utilized as a negative control (JZ-172). When the O.D. reached around 0.5, the culture was cooled to various temperatures (18° C.-37° C.). 50 ng/mL of anhydrotetracycline (aTc) was added for protein production and GABA was supplied to a final concentration of 0-10 mM. The 2-pyrrolidone titer was analyzed 24 h after induction.

2.8.2 Inducible 2-pyrrolidone Production from Glutamate

E. coli strains (JZ-336~JZ-353, JZ-371~JZ-380, JZ-386) carrying both glutamate decarboxylase and GABA activating enzyme expression plasmids were inoculated in 25 mL LB medium containing various concentrations of glutamate (0 to 9 g/L) with appropriate antibiotics and grown at 37° C. When O.D. reached around 0.6, the culture was cooled to 25° C. IPTG and aTet were added to a final concentration of 500 µM and 50 ng/mL, respectively to induce protein expression. The pH was titrated by adding 0.6N HCl solution, and the culture was placed in a 25° C. incubator. 2-Pyrrolidone titer was analyzed at 24 h after induction.

2.8.3 Autoinducible 2-pyrrolidone Production from Glutamate

E. coli strains (JZ-344, JZ-386) carrying both glutamate decarboxylase and GABA activating enzyme expression plasmids were inoculated into 10 mL of LB or LB plus 5 g/L glutamate overnight. On day 2, the overnight culture was inoculated 1:100 (v/v) into 25 mL Studier's autoinduction ZYM-5052 medium with various concentrations of glutamate (0 g/L to 9 g/L) and appropriate antibiotics(Studier 2005). The culture was incubated at 37° C. When the O.D. reached around 0.6, the culture was cooled to 25° C. The pH was titrated to 5.25 by adding 0.6N HCl solution. The culture was then placed at 25° C. incubator and 2-pyrrolidone titer was analyzed at 24 h later.

3. Results 3.1. GABA Activation Enzyme Candidates

Figure 8A:
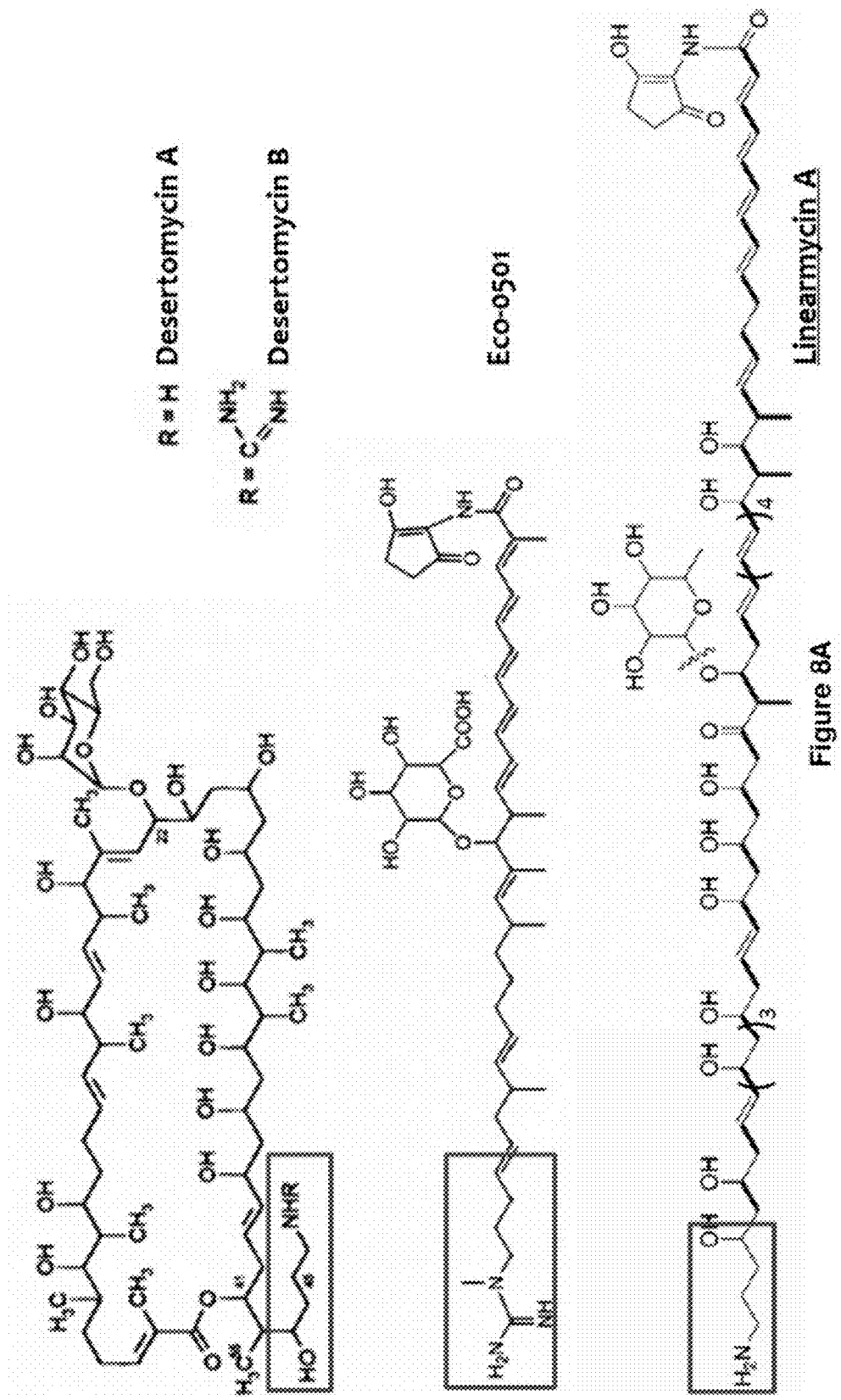
FIG. 8A. Linearmycin A structure for linearmycin A biosynthesis. The structure of natural products that contain 4-aminobutyrate like starter unit, Desertomycin A/B, Eco-0501, linearmycin A. B) genomic arrangement of the locus coding for linearmycin A PKS aglycone biosynthesis. Open reading frame (ORFs) 10 through 18 encode the type I polyketide synthase, the predicted domains of these ORFs are shown. Two ORFs in the gene cluster, ORF27 and ORF36, were predicted to be AMP-dependent synthetases.
Figure 8B:
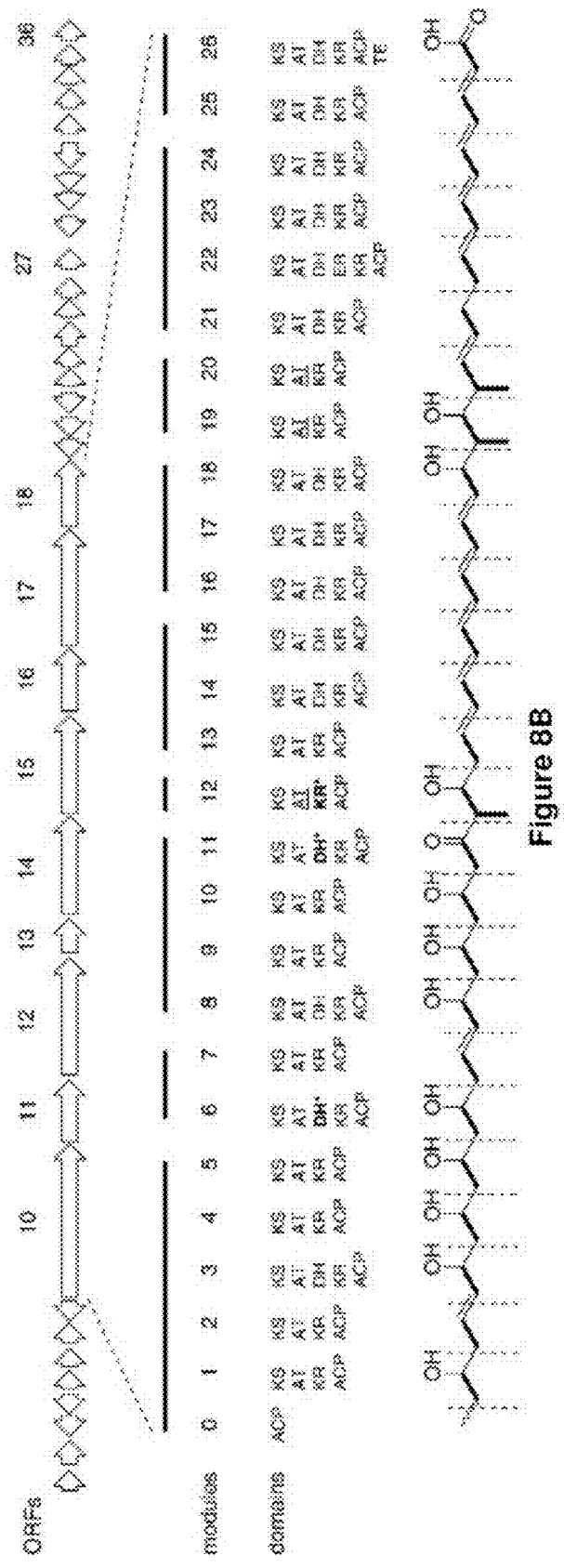
FIG. 8B. Genomic arrangement of the locus coding for linearmycin A PKS aglycone biosynthesis. Open reading frame (ORFs) 10 through 18 encode the type I polyketide synthase, the predicted domains of these ORFs are shown. Two ORFs in the gene cluster, ORF27 and ORF36, were predicted to be AMP-dependent synthetases.

Twenty four polyketides with amine containing polyketides were screened using retrobiosynthetic analysis: Vecinistatin, 13-Desmethyl Spirolide C, chejuenolides A and B, oxazolomycins, bacillaene, myxovirescin A, onnamides, virginiamycin M, kirromycin, pederin, etnangien, stellattamide-A, Myxalamids, tolytoxin, salinilactam, MLL-449, hitachimycin, leinamycin, lankacidin, indanomycin, BE-14106, desertomycin A and B, Eco-0501, linearmycin A and Eco-02301. Among them, desertomycin A, linearmycin A and Eco-02301 have a GABA-containing C4 amine starter unit, and linearmycin A has the biosynthetic PKS gene cluster sequence information available (FIG. 8) (Sakuda, Guce-Bigol et al. 1996, Zazopoulos, Huang et al. 2003, James B. McAlpine 2005, Wenjun Zhang 2010). Two ORFs in the gene cluster, ORF27 and ORF36, were predicted to be AMP-dependent synthetases(Bachmann 2008). ORF36 was highly homologous to a previously identified 5-aminolevulinyl-CoA synthase responsible for 2-amino-3-hydroxycyclopent-2-enone five membered ring formation during Eco-02301 biosynthesis(Wenjun Zhang 2010). So ORF27 is likely to be involved in activation of the GABA starter unit loading, which made it the best candidate for 2-pyrrolidone synthase.

3.2. ORF27 Catalyzes GABA to 2-pyrrolidone Formation In Vitro

Figure 2A:
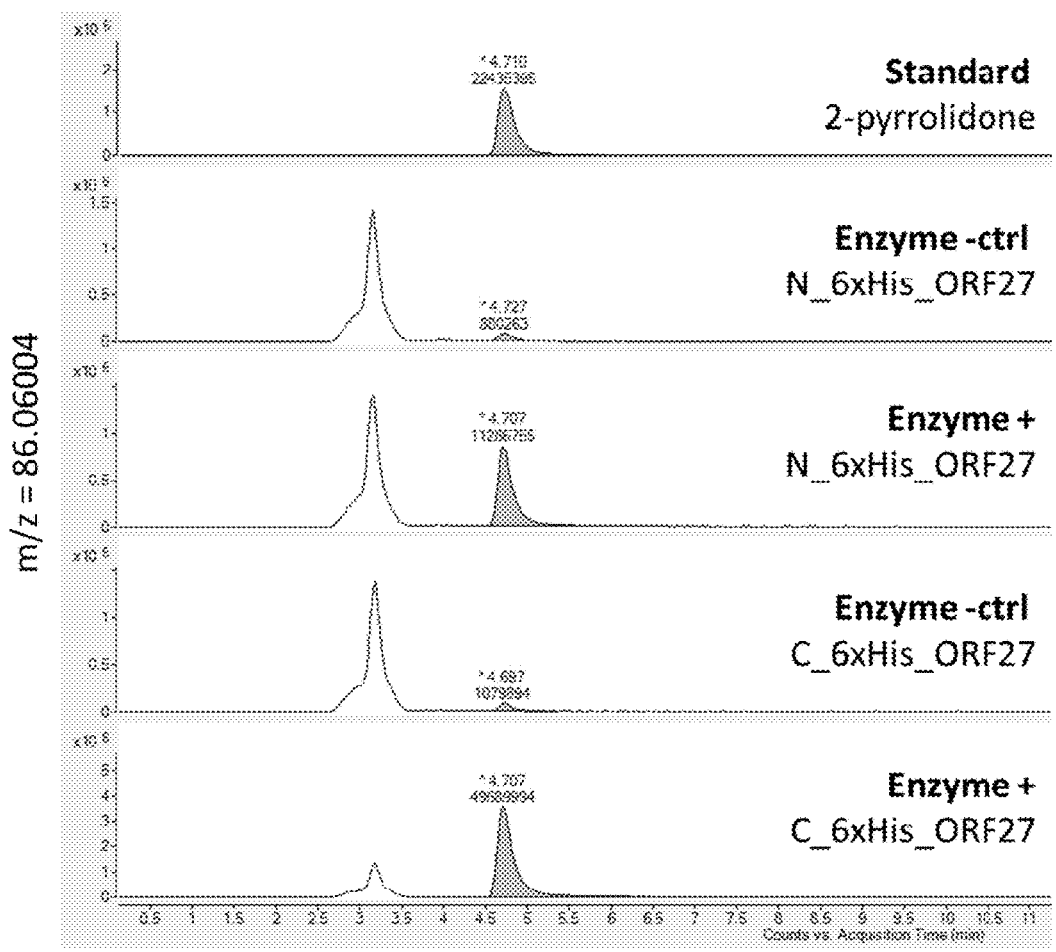
FIG. 2A. LC-MS Chromatogram for in vitro 2-pyrrolidone formation catalyzed by N-6×His-ORF27 and C-6×His-ORF27. 2-pyrrolidone elutes at around 4.71 $min^1$.
Figure 2B:
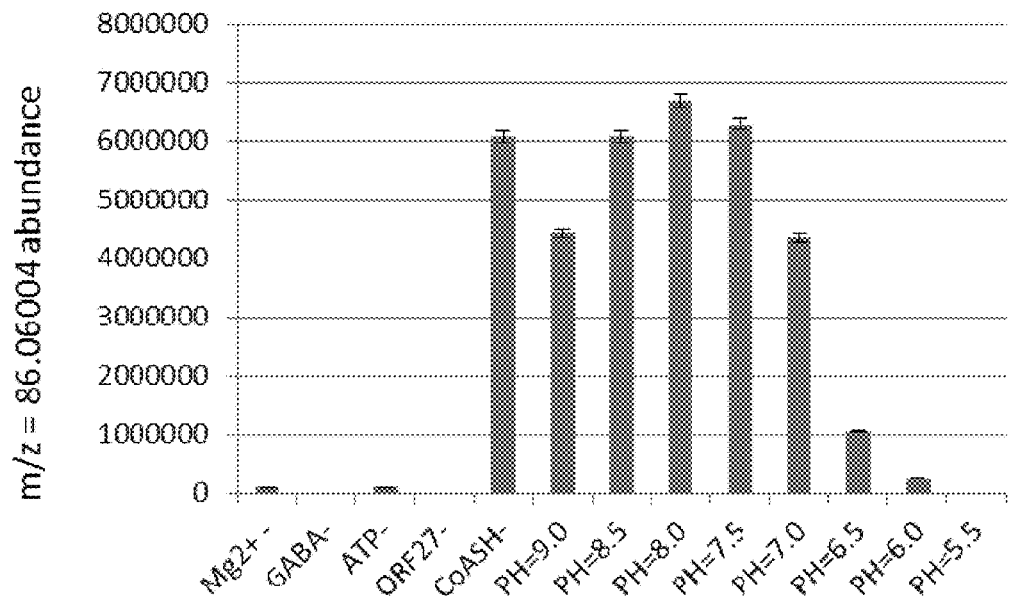
FIG. 2B. in vitro 2-pyrrolidone formation catalyzed by ORF27 in an ATP dependent manner, also in vitro pH dependent kinetic profile of ORF27 catalyzed 2-pyrrolidone formation. Note: the 3.2 min peak is likely a dehydration product during GABA ionization.

Both purified N-terminal 6×His ORF27 and C-terminal 6×His ORF27 were able to activate GABA's carboxyl group and result in the formation of 2-pyrrolidone (FIG. 2A). Even though ORF27 is predicted to be an acyl-CoA ligase, CoASH is not required for 2-pyrrolidone formation. The minimal reaction system constitutes GABA, enzyme ORF27, ATP and $Mg^{2+}$ (FIG. 2B). No 4-aminobutyryl-CoA was detected when CoASH's was added to the reaction. Mass ions corresponding to other off-pathway products, such as the GABA dimer, were also not observed. The pH profile of ORF27 activity was determined, and the enzyme has a pH optimum of 8.0. The enzyme precipitates and becomes inactive when the pH drops below 6.0.

3.2.1 ORF27 and E. coli's Native CaiC Catalyze 2-pyrrolidone Formation In Vivo

Figure 3:
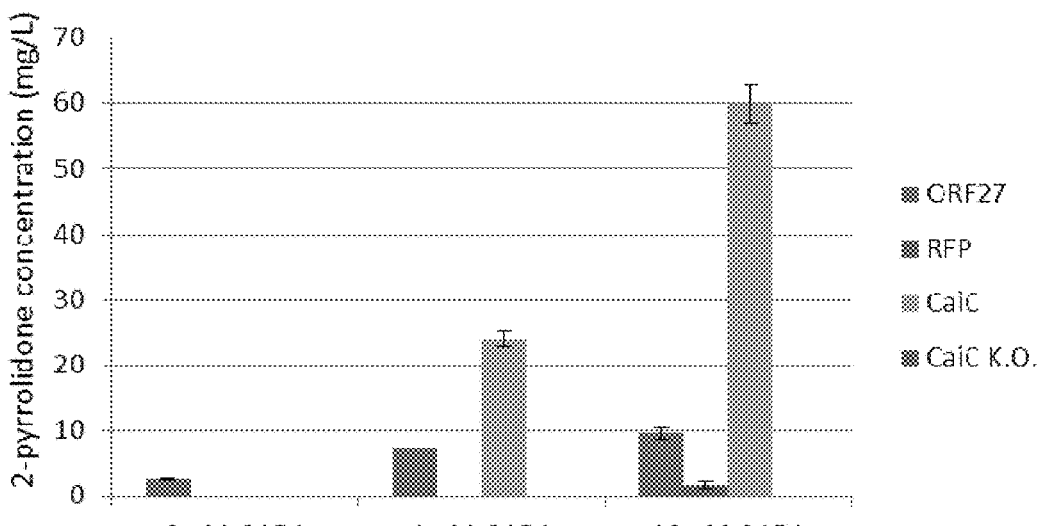
FIG. 3. 2-Pyrrolidone production in vivo, catalyzed by overexpression of enzyme ORF27 and *E. coli*'s native CaiC. As the caiC gene is knocked out, 2-pyrrolidone is not observed in the RFP control.

E. coli JW2637-4 from the KEIO knockout library contains a knockout of gabT, which encodes a GABA transaminase involved in GABA catabolism(Baba, Ara et al. 2006). This host was initially used to confirm production of 2-pyrrolidone in vivo. E. coli JZ-298 (ORF27), and JZ-172 (RFP negative control) were grown in LB medium containing 0, 1, and 10 mM GABA (FIG. 3). At 0 mM and 1 mM GABA, 2-pyrrolidone was observed only in the presence of ORF27. Surprisingly, at 10 mM GABA, slight 2-pyrrolidone production was observed in the RFP control strain, indicating that nonspecific catalysis of GABA by a native E. coli enzyme also contributes to 2-pyrrolidone formation. Various AMP activating enzymes were cloned and overexpressed, among them CaiC overexpression lead to 2-pyrrolidone formation(Bernal, Arense et al. 2008). E. coli JW0036-1, the KEIO collection caiC deletion mutant, was transformed with pBbE2C-RFP, creating strain E. coli JZ-393, which overexpresses RFP; this strain was no longer able to produce 2-pyrrolidone when fed 10 mM GABA (FIG. 3).

Figure 4:
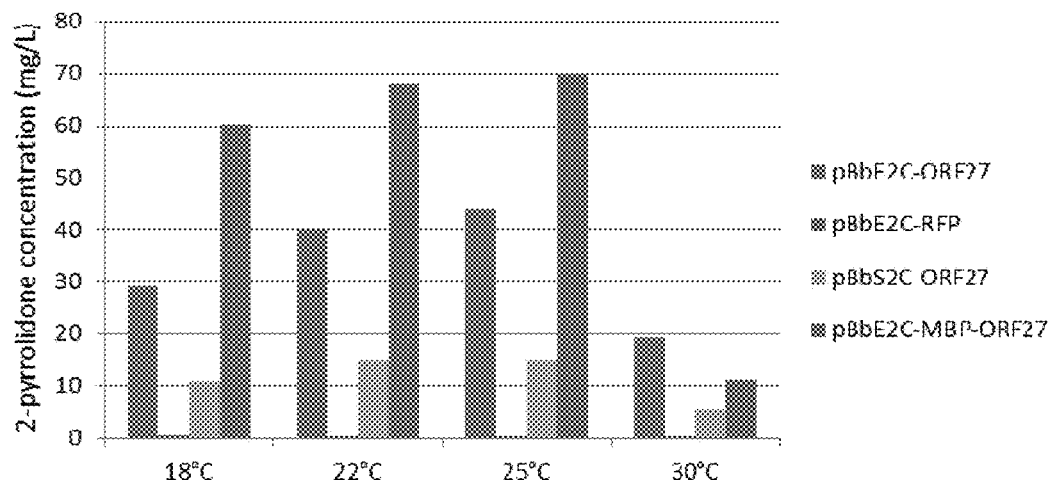
FIG. 4. Optimization of copy number, temperature and ORF27 solubility for 2-pyrrolidone production from 100 mM GABA. Expression of the MBP-fusion of ORF27 from high copy number plasmids at 25° C. gave the optimal 2-pyrrolidone titer.
Figure 9A:
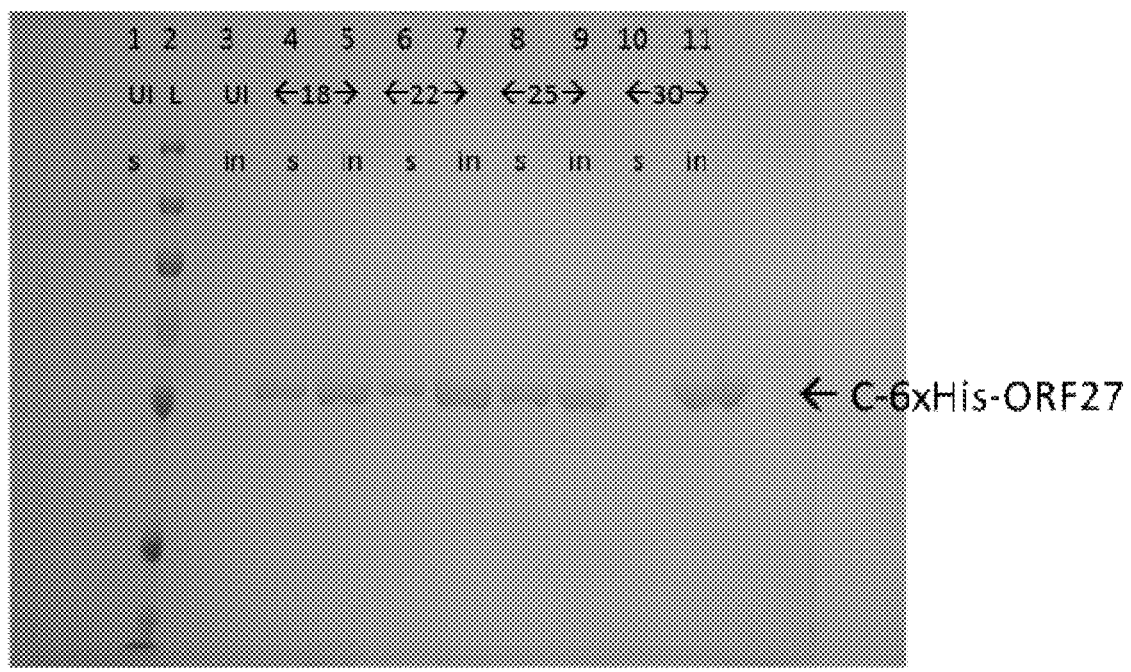
FIG. 9A. Time dependent expression solubility of C-6× His-ORF27. Day 1, solubility of C-6×His-ORF27 expression at various temperatures.
Figure 9B:
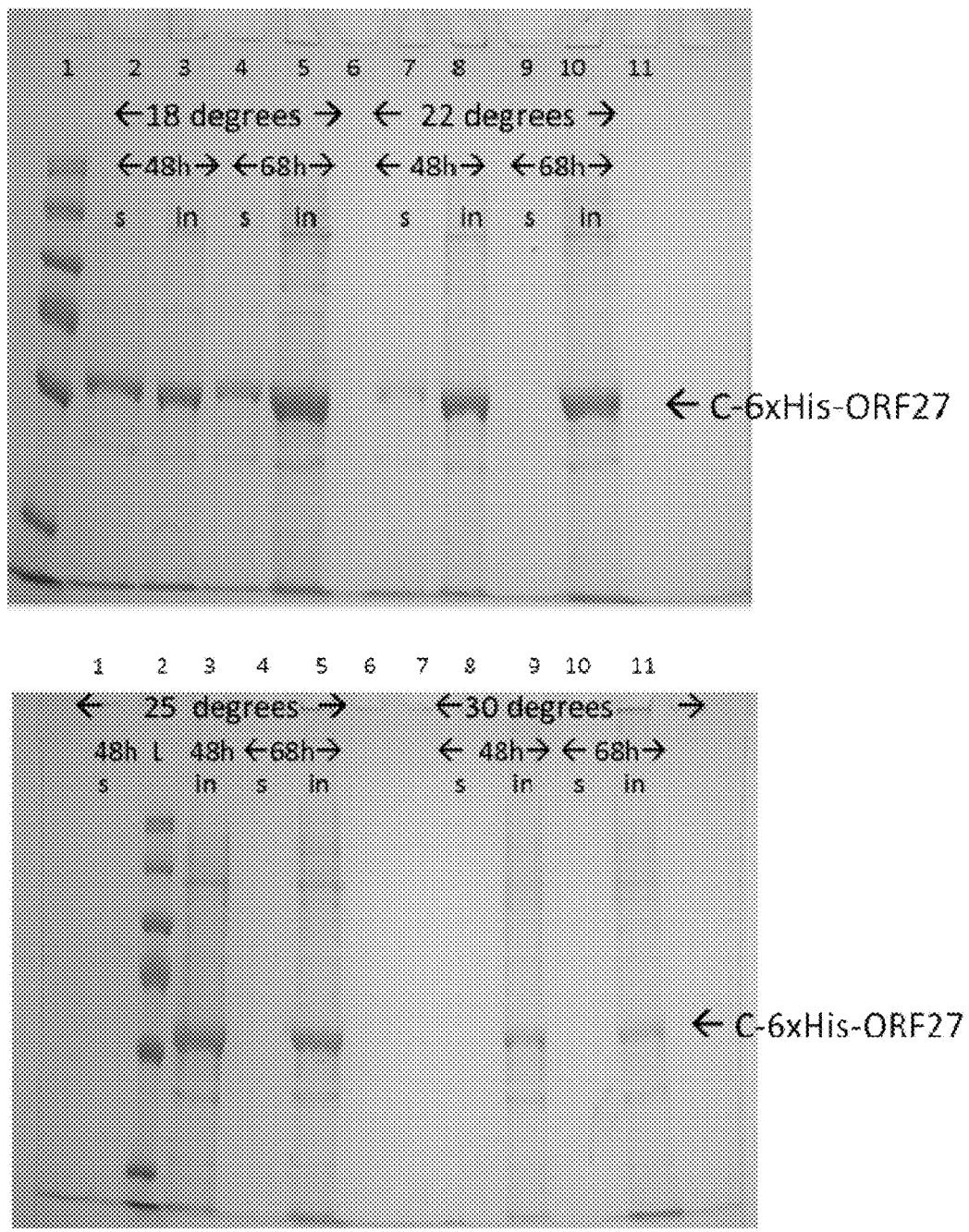
FIG. 9B. Time dependent expression solubility of C-6× His-ORF27. Day 2 and day 3, aggregation of C-6×His-ORF27 in various temperatures.

3.2.2 Increased ORF27 Functional Expression Improves GABA to 2-pyrrolidone Conversion In Vivo Although both versions of the N- and C-terminal Histagged ORF27 were expressed solubly at 30° C., ORF27 had the tendency to aggregate and become insoluble one day after induction depending on the temperature (FIGS. 9A and 9B). CaiC may have higher thermostability and can be functionally expressed at 37° C. By balancing reaction rate and enzyme functional expression, the optimal temperature was determined to be 25° C. for both enzymes to maximize 2-pyrrolidone titer from GABA. The MBP fusion increased ORF27's protein solubility and resulted in a 2× improvement in overall titer (FIG. 4). This strategy did not prevent ORF27's protein aggregation though. An MBP fusion with CaiC had a slight incremental impact on the 2-pyrrolidone titer from GABA due to CaiC's innate higher thermostability. To test whether MBP-ORF27 overexpression may cause aggregation, thus toxicity for the cell, a low copy number plasmid harboring the SC101 origin of replication and MBP-ORF27 was tested. However, use of this plasmid decreased the titer (FIG. 4), presumably due to lower expression of the enzyme.

CH184 is an E. coli strain with slow ribosome translation rate (T. Ruusala 1984). Previous studies showed that this is a good host for expression of multidomain proteins with poor solubilities, presumably a result of co-translational folding of multidomain proteins (T. Ruusala 1984, Fluitt, Pienaar et al. 2007, Proshkin, Rahmouni et al. 2010, Siller, DeZwaan et al. 2010). However, its slow growth rate and its inability to improve MBP-ORF27 solubility indicated that CH184 would not be a useful host for 2-pyrrolidone production.

Figure 5A:
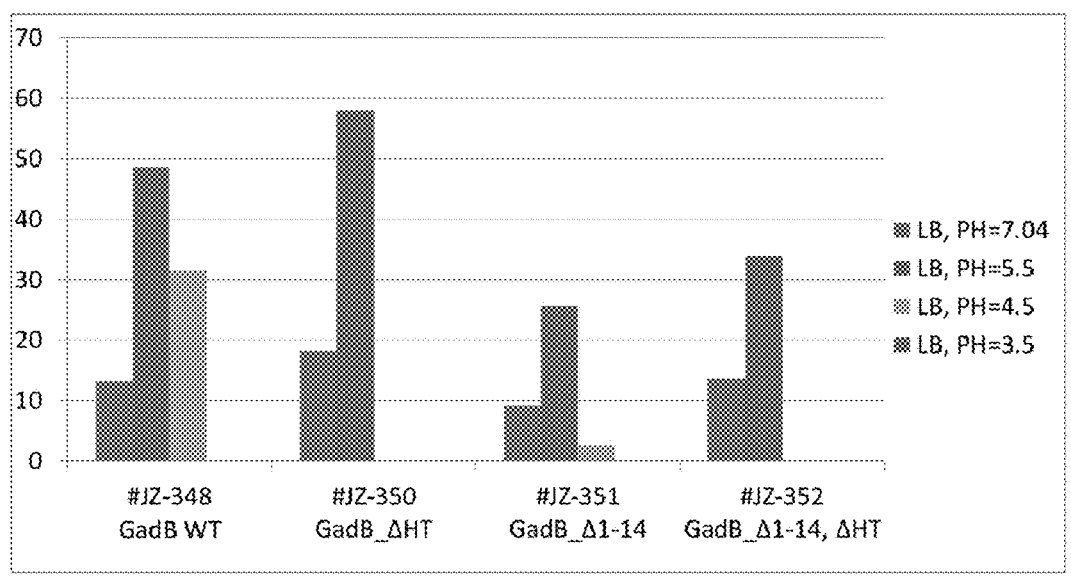
FIG. 5A. GadB mutants and the effect of extracellular pH on 2-pyrrolidone titer when feeding 10 mM glutamic acid.
Figure 5B:
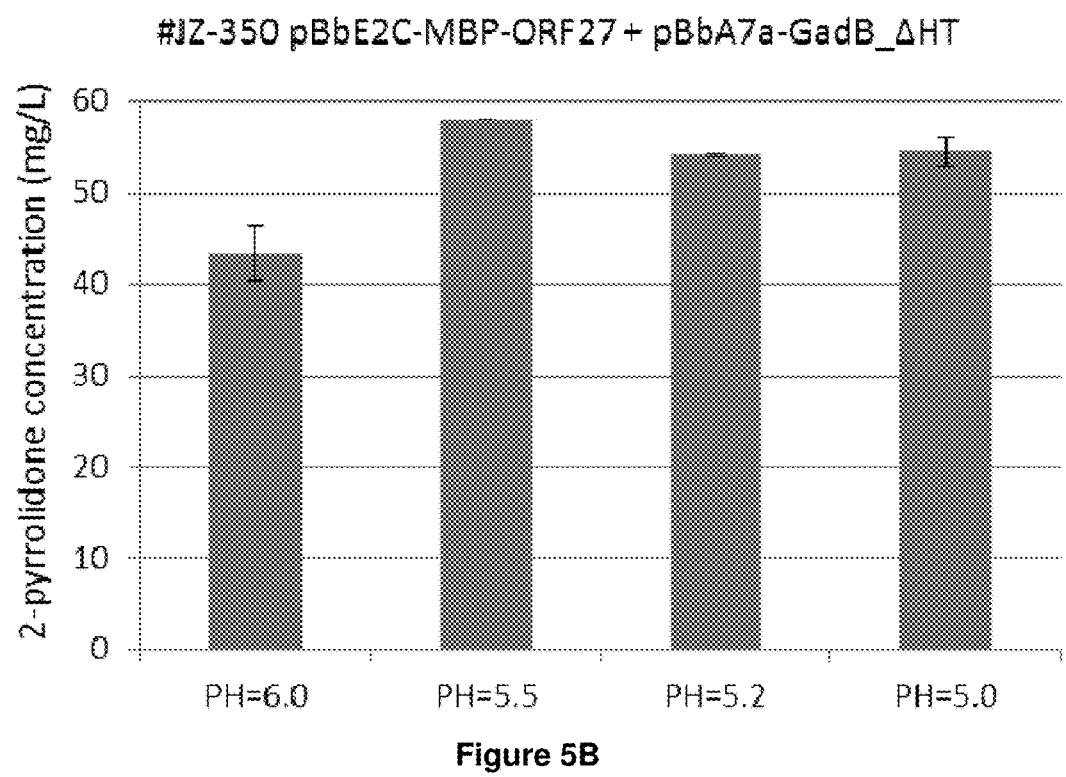
FIG. 5B. pH sensitivity analysis for 2-pyrrolidone production from pH=5.0 to 6.0.

3.3 Inducible 2-pyrrolidone Production from Glutamate 3.3.1 pH Profile Experiment A two-step 2-pyrrolidone biosynthetic route from glutamate consists of the E. coli glutamate decarboxylase candidate GadB and MBP-ORF27 as the 2-pyrrolidone synthase. Not only would the first enzymatic step in the pathway significantly increase the pH of the growth medium, but the two enzymes have a drastic 4.2 pH unit difference in their pH optima as well. In native E. coli, production of GABA from glutamate is utilized as an acid resistance mechanism, and GadB is activated under acidic conditions(1999, Capitani G 2003). GadB has a pH optimum of 3.8 and its catalytic activity significantly decreases when pH goes above 5.0 (Pennacchietti, Lammens et al. 2009). Previous *E. coli* GABA overproduction studies using GABA biosynthesis from glutamate as a substrate were performed at pH=3.5(Le Vo, Kim et al. 2012, Park, Kim et al. 2013). The huge pH profile gap of the two enzymatic steps can be challenging for a one pot reaction. Indeed, initial inducible 2-pyrrolidone production trials at pH=3.5 with an integrated pathway (*E. coli* strain JZ-337) resulted in *E. coli* cell lysis and no 2-pyrrolidone production. GadB histidine[465] plays an important role at pHs near neutral; GadB mutants, such as H465A or ΔHT, enable GadB to maintain its relatively high activity at more alkaline pH (Pennacchietti, Lammens et al. 2009). As shown in the extracellular pH profile for 2-pyrrolidone biosynthesis strains carrying wild type and mutant GadB (JZ-336, JZ-338), pH~5.5 resulted in the highest 2-pyrrolidone titer for both GadB variants (FIG. 5A). Δ1-14 mutants, which contain a deletion of N terminal peptide responsible for recruiting the GadB hexamer to the membrane, performed slightly worse than their counter parts(Capitani G 2003). Sensitivity analysis showed that strains carrying GadB ΔHT robustly gave optimum yield within the pH range of 5.0-5.5, and declined when the exogenous pH drifted above 6.0 or below 4.5 (FIG. 5B). A gabT knockout, which eliminates GABA transaminase, had little impact on the titer.

3.3.2 Promoter Engineering and Chaperone Co-Expression

Figure 5C:
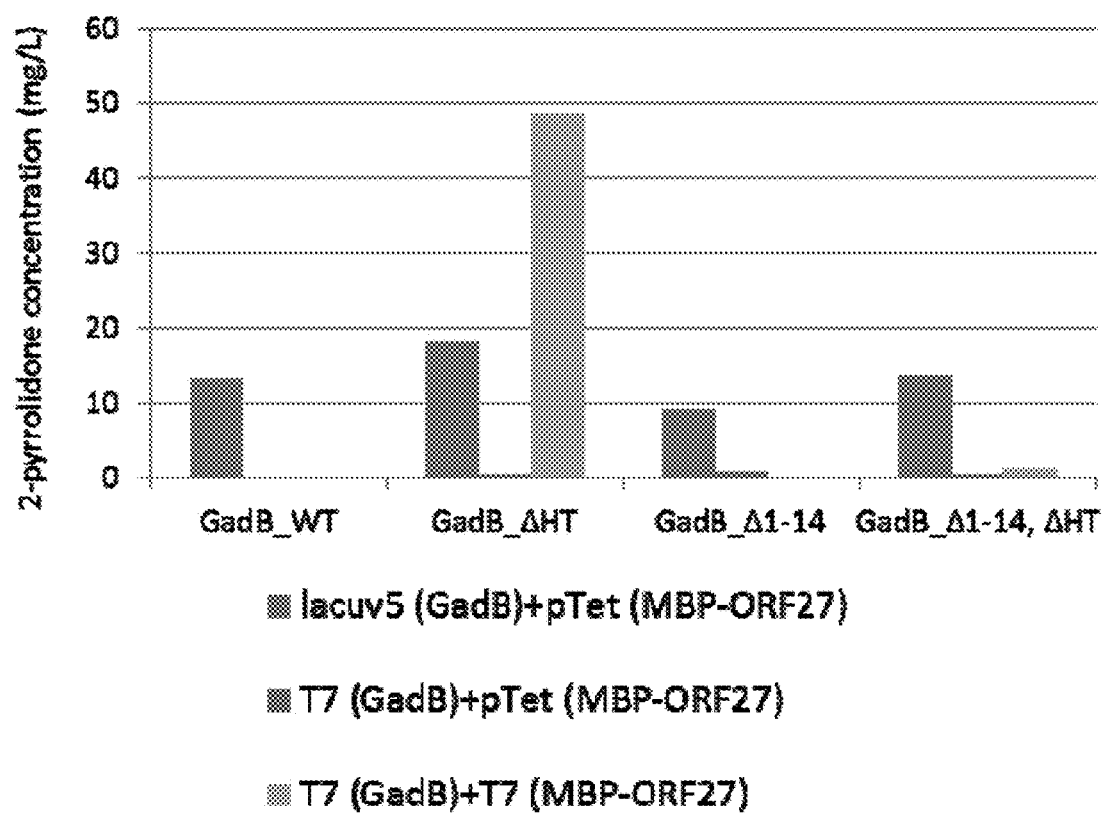
FIG. 5C. The effect of promoter strength on 2-pyrrolidone titer when feeding 10 mM glutamic acid at an extracellular pH of 7.0.
Figure 6:
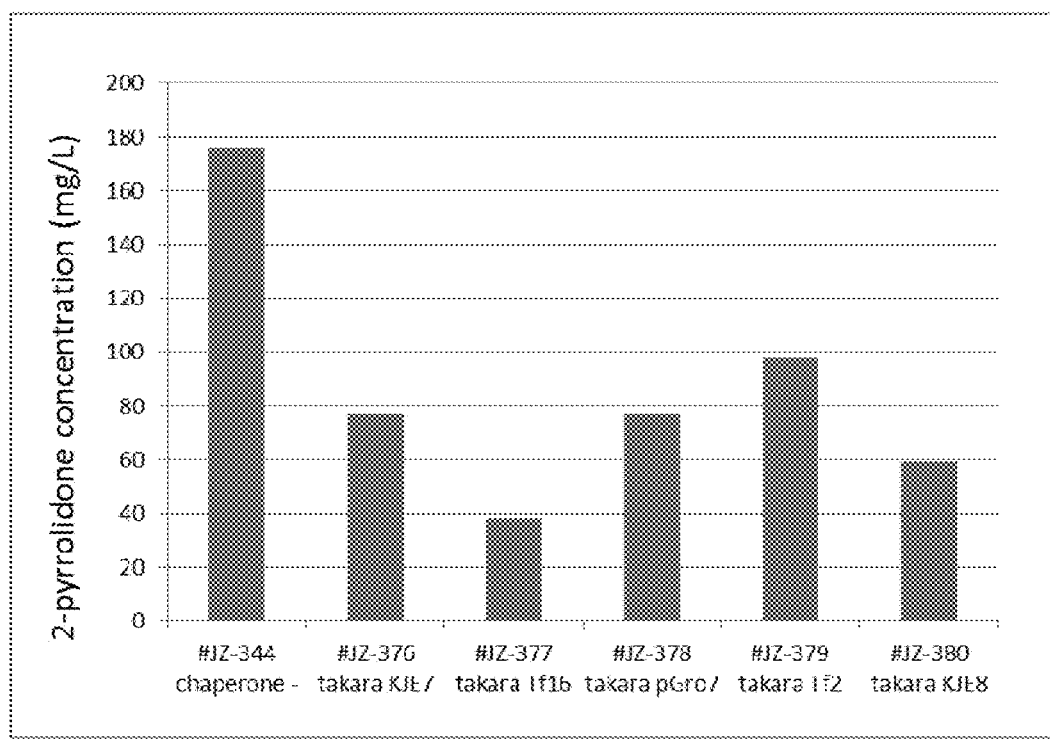
FIG. 6. Effect of chaperone coexpression on titer when feeding 10 g/L glutamic acid (~68 mM) in LB media.

To increase the flux through the pathway, various inducible promoters were tested (JZ-336 and JZ-338, JZ-342 to 344, JZ-348 to 350). Production of 2-pyrrolidone was highest when strong promoters were used, so the T7 promoter was chosen to drive expression of GadB ΔHT and MBP-ORF27 for optimal 2-pyrrolidone production (FIG. 5C). The full set of Takara chaperones were tested (JZ-371 to 380) to determine if chaperone proteins would increase the titer by alleviating MBP-ORF27 aggregation, and in all cases, the titer decreased between 20% to 85% (FIG. 6) (Kazuyo Nishihara 1998, Kazuyo Nishihara 2000).

3.4. Autoinducible 2-pyrrolidone Production from Glutamate

Figure 7A:
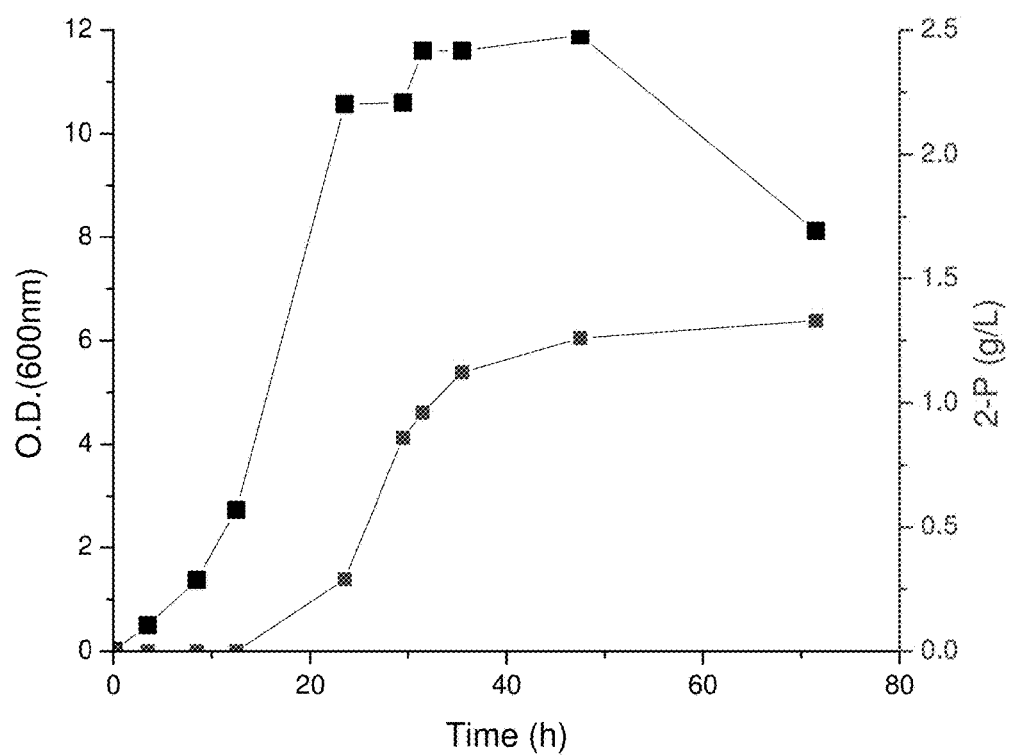
FIG. 7A. *E. coli* strain #344 Production 2-pyrrolidone from glutamic acid (red squares) and O.D. of *E. coli* growth (black squares).
Figure 7B:
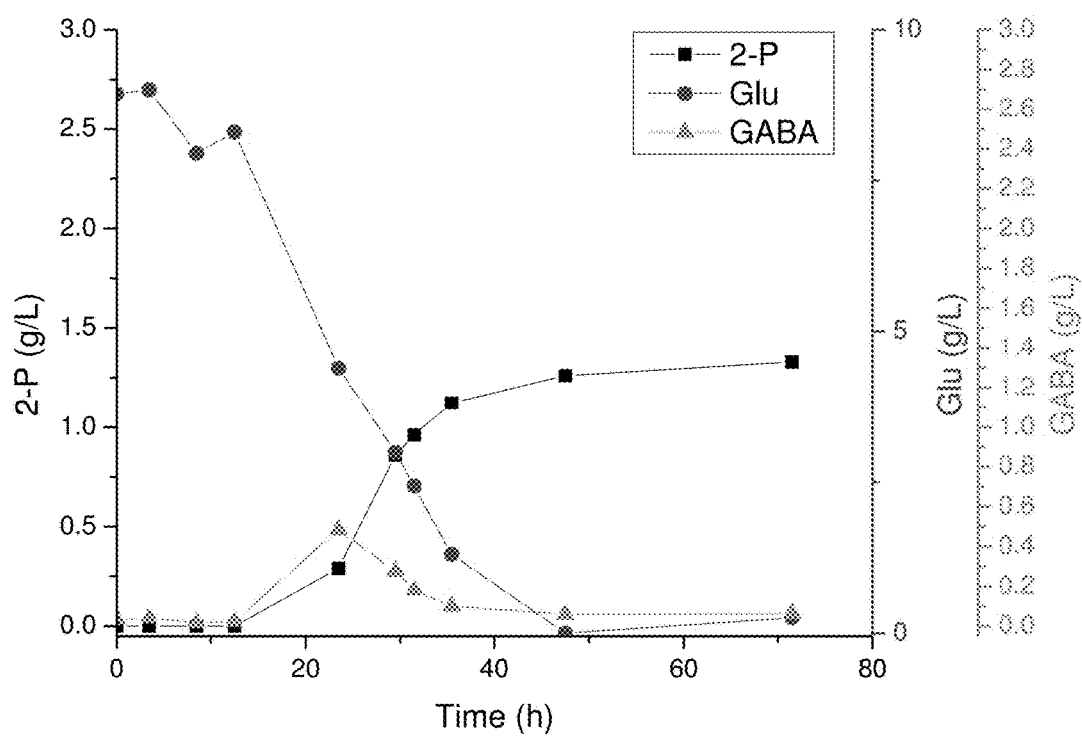
FIG. 7B. Glutamic acid feed consumption, GABA intermediate accumulation and 2-pyrrolidone generation.
Figure 10:
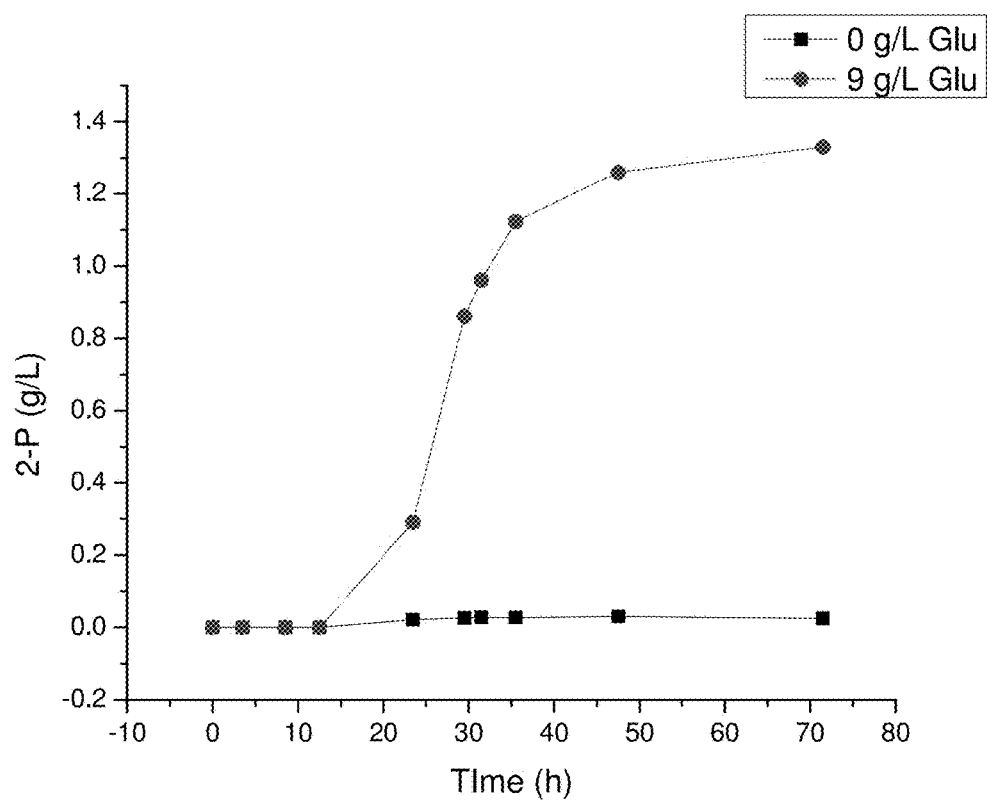
FIG. 10. High density culture 2-pyrrolidone production derives mostly from glutamic acid feeding rather than carbon and nitrogen source in Studier's ZYM-5052 media.
Figure 11:
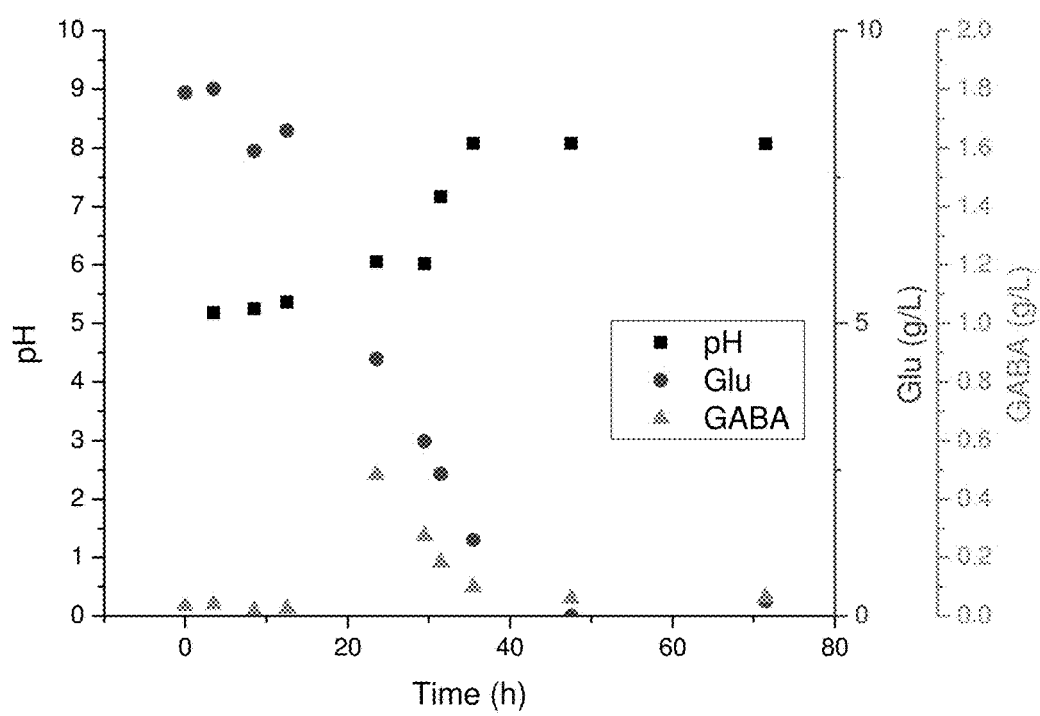
FIG. 11. pH change during the fermentation process, glutamate consumption and GABA intermediate accumulation.

Studier's ZYM-5052 is a high density culture medium that enables autoinduction of protein expression in *E. coli* (Studier 2005). Strain JZ-344, grown overnight LB medium, was tested through 2-stage autoinducible 2-pyrrolidone production from glutamate: stage I, cell growth to O.D.~0.6 at 37° C.; stage II, pH titration to 5.25 and incubation at 25° C. for 2-pyrrolidone production. Fermentation in medium with 9 g/L and 0 g/L of glutamate showed that over 98% of 2-pyrrolidone was converted from glutamate supplied in the medium (FIG. 10). Overall, 1.1 g/L of 2-pyrrolidone was produced by converting 7.7 g/L of L-glutamate within 31 h, achieving 25% conversion (FIG. 7A). The formation of GABA intermediates occurred rapidly during the first 30 h. During this time, the pH increased from 5.25 to 8.07 and occurred mainly during the glutamate to GABA conversion period (FIG. 11). There was an approximate 6-hour time delay between extracellular GABA accumulation and 2-pyrrolidone formation. GABA was rapidly transformed into 2-pyrrolidone when MBP-ORF27 was solubly expressed in day 1. 2-Pyrrolidone formation slowed down when MBP-ORF27 started to aggregate at around 48 h time point (FIG. 7B). The OD of culture decrease from 12 to 8, presumably due to cell lysis as a result of the high pH.

3.5 Cofactor Supplementation and *E. coli* CaiC

PLP is a cofactor for glutamate decarboxylase activity (Capitani G 2003, Pennacchietti, Lammens et al. 2009, Takahashi, Shirakawa et al. 2012); 1 mM, 0.1 mM and 0 mM of PLP supplementation were compared. PLP supplementation had little impact on 2-pyrrolidone yield; either the first decarboxylation step was not limited by cofactor or glutamate decarboxylation was not the rate limiting step.

*E. coli* CaiC was also tested(Bernal, Arense et al. 2008). Although CaiC has better thermostability and outperformed ORF27 in 2-pyrrolidone biosynthesis during GABA feeding, expression of *E. coli* CaiC conferred more growth stress under glutamate feeding conditions, and resulted in only 18.7% of the 2-pyrrolidone titer of that achieved when engineered ORF27 fused with MBP was used.

4. Discussion

Through years of engineering, the petrochemical industry created over 4,000 bulk chemicals (from ICIS). This dwarfs the chemicals produced via fermentation. Currently, around 200 products are made via microbial fermentation (excluding food and beverages), including amino acids, bioactive compounds, etc. However, with advances in synthetic biology, it is now possible to engineer microbes to produce chemicals traditionally made via petrochemical processes at lower cost. Due to the differences in raw material and chemistry, the petrochemical processes may be advantaged for relatively simple, symmetric and reduced compounds, yet they cannot match microbial processes when it comes to highly functionalized compounds with higher oxidation states.

An important step towards building molecules of increasing complexity is to discover enzymes for substrate activation, such as C—C bond and C—N bond formation (Dougherty and Arnold 2009). Although directed evolution has been applied to modify enzymes for novel substrate recognition, these methods usually require high throughput assays, and the engineered enzyme often suffers from relatively low efficiency and turnover number(Dougherty and Arnold 2009, Dietrich, McKee et al. 2010, Esvelt, Carlson et al. 2011). Unfortunately, bioinformatics prediction of an enzyme's substrate is still in its infancy. Here we successfully demonstrated an efficient methodology to scout for enzymes from the secondary metabolite linearmycin A biosynthetic gene cluster that activate γ-aminobutyrate. The huge diversity of secondary metabolites and the functional groups embedded in these molecules made them a rich source of gene candidates (Yadav, Gokhale et al. 2009, Medema, Breitling et al. 2011). Polyketide biosynthesis follows the colinearity rule and is highly predictable in terms of its biosynthetic pathway, making them useful source of substrate activating enzymes.

The discovery of *S. aizunensis* ORF27 enables the first demonstration of 2-pyrrolidone production from γ-aminobutyrate at mild fermentation conditions. Although the dehydration of γ-aminobutyrate to form 2-pyrrolidone is thermodynamically favorable, due to its high activation barrier, a significant temperature (>200° C.) is required for the reaction to proceed even in the presence of $Al_2O_3$ catalyst. This reaction requires several days to complete, and the harsh conditions also lead to off pathway reactions, producing oligomers or cyclic GABA dimer or trimer(Stavila and Loos 2013). The enzyme ORF27 utilize ATP to activate the γ-aminobutyrate, presumably generating the labile γ-aminobutyryl ester intermediate, which rapidly cyclizes to form 2-pyrrolidone.

*S. aizunensis* ORF27 belongs to the AMP-activating enzyme family. This didomain enzyme was prone to aggregation when heterologously overexpressed in *E. coli*. Previously, SUMO, but not MBP fusion, has been used in metabolic engineering to improve enzyme solubility and increase product titers(Shiue and Prather 2014). In our case, utilizing the MBP fusion alleviated ORF27 aggregation and maintained enzymatic activity for prolonged 2-pyrrolidone production, thus leading to an increased final titer. Since functional heterologous expression of enzymes such as P450s, terpene synthases, and polyketide synthases in microbial hosts is a major bottleneck, fusion with solubilizing domains can be a general metabolic engineering strategy.

The surprising 2-pyrrolidone synthase activity of native CaiC in *E. coli* highlights the unintended cross talk during metabolic engineering. In the case of CaiC, previous research concluded that GABA was not CaiC's substrate judging from CoA product assay(Bernal, Arense et al. 2008). While substrate profiling for enzymes in the engineered pathway are commonly done to identify "enzyme hijacking" by other intracellular metabolites, little attention was paid to the "enzyme profiling" of metabolic engineering pathway intermediates, and the impact of "substrate hijacking of host enzymes" on microbial growth or product titer. Traditional biochemical characterization of enzymes aims to identify native substrates and perform substrate screening under sub-millimolar conditions. Activities on substrate analogs or competitive inhibition studies were also performed under similar conditions. However, during metabolic engineering of microbial chemical production, intermediate concentrations can increase to submolar or even molar levels. Also, there is a significant difference between the intracellular environment and in vitro assay environment, such as salt concentration, crowdedness, etc. This can lead to unknown and unwanted side reactions, which can reduce yields and create toxic metabolites(Kizer, Pitera et al. 2008). For instance, CaiC was reported to have negative activity on GABA in vitro assays. Luckily in our case, caiC is not essential for *E. coli*, and caiC KO did not impact growth. Therefore caiC's competitive inhibition by GABA did not cause a growth defect. However, it is generally necessary to conduct a thorough investigation and check for side activity against intermediates for all enzyme classes of the same family in a native microbial host.

As mentioned previously, metabolic engineering is more than simply recruiting various enzymes to the same host (Chaitan Khosla 2003). Enzymes are historically evolved to operate under drastically different conditions(Galperin and Koonin 2012). In our two enzymatic reactions steps, the pH optimum of *E. coli* wild type GadB and *S. aizunensis* ORF27 differ by a dramatic 4.2 pH units, making it almost impossible to perform a one-pot reaction with the two catalysts. Wild type GadB loses 83% of its activity when the pH reaches 6.0 (*S. aizunensis* ORF27 precipitates), and almost completely loses its activity at pH=6.5 (ORF27 maintains 20% of its optimum activity when pH drop to 6.5). Protein engineering shrunk the gap between the pH profiles, and enabled the complete 2-pyrrolidone biosynthetic pathway from glutamate.

In considering overall limitations on the productivity of this system, MBP-ORF27 is the rate limiting step, and the enzyme suffers from a tendency to aggregate. It would be desirable to evolve ORF27 to be more soluble and stable so that prolonged 2-pyrrolidone biosynthesis can be sustained during production process. On the other hand, our study opened the door for microbial 2-pyrrolidone production, transferring the pathway into other glutamate overproduction hosts such as *Corynebacterium glutamicum* are currently under investigation.

5. Conclusion

In this study, we utilized retro-biosynthetic analysis of polyketide natural products as a targeted method to prospect for novel γ-aminobutyrate activating enzymes for performing unprecedented reactions such as GABA conversion to 2-pyrrolidone. *E. coli*'s native CaiC, a betaine-CoA ligase, was also discovered to be able to catalyze 2-pyrrolidone formation. Protein modification, such as MBP fusion, increased the activity of expressed ORF27. The GadB ΔHT mutant shrunk the pH differences between the two enzymatic steps. Metabolic engineering and process optimization collectively improved 2-pyrrolidone titer from glutamate. 1.1 g/L of 2-pyrrolidone was produced from 9 g/L of glutamate, representing a 25% conversion.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell comprising a 2-pyrrolidone synthase comprising an amino acid sequence having at least 80% identity with SEQ ID NO:1, wherein the amino acid sequence comprises one or more of the following conserved amino acid motifs or sites: acyl-activating enzyme (AAE) consensus motif (residues 137, 140-145, and 147-148), acyl-activating enzyme (AAE) consensus motif (residues 140, 257-258, 279-284, 357, 369, 372, 382, and 458), AMP binding site (residues 140, 180-181, 227, 229-230, 233, 257-258, 279-284, 357, 369, 372, 379-382, and 439), and CoA binding site (residues 180, 229-230, 233, 257, 379-381, 433, and 439) heterologous to the host cell, wherein the 2-pyrrolidone synthase catalyzes the following reaction:

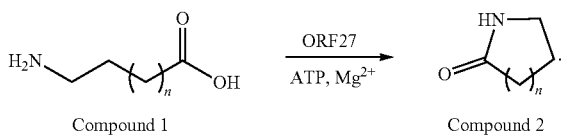

2. The genetically modified host cell of claim 1, wherein host cell is capable of synthesizing Compound 1 or uptaking Compound 1 from the environment or culture.

3. The genetically modified host cell of claim 2, wherein host cell further comprises one or more enzymes of a pathway for synthesizing Compound 1 from a carbon source.

4. The genetically modified host cell of claim 3, wherein pathway for synthesizing Compound 1 from a carbon source that is native to the host cell.

5. The genetically modified host cell of claim 3, wherein pathway for synthesizing Compound 1 from a carbon source is heterologous to the host cell.

6. The genetically modified host cell of claim 1, wherein host cell lacks betaine-CoA ligase.

7. The genetically modified host cell of claim 1, wherein n is an integer from 1 to 20.

8. The genetically modified host cell of claim 7, wherein n is an integer from 1 to 10.

9. The genetically modified host cell of claim 8, wherein n is an integer from 1 to 7.

10. The genetically modified host cell of claim 9, wherein n is an integer from 1 to 3.

11. A method of producing a Compound 2 in a genetically modified host cell, comprising:

(a) providing the genetically modified host cell of claim 1,
(b) culturing the genetically modified host cell in a medium under a suitable condition such that the culturing results in the genetically modified host cell producing a Compound 2.

12. The method of claim 11, further comprising introducing one or more nucleic acid(s) into the host cell encoding the enzyme operably linked to a suitable promoter capable of transcription in the host cell, and optionally encoding the one or more enzyme(s) of a pathway for synthesizing Compound 1 from a carbon source; wherein the introducing step is prior to the culturing step.

13. The method of claim 11, further comprising separating Compound 2 from the host cell and/or the medium, wherein the separating step is subsequent, concurrent or partially concurrent with the culturing step.

14. The genetically modified host cell of claim 1, wherein the 2-pyrrolidone synthase comprising an amino acid sequence comprising the following conserved amino acid motifs or sites: acyl-activating enzyme (AAE) consensus motif (residues 137, 140-145, and 147-148), acyl-activating enzyme (AAE) consensus motif (residues 140, 257-258, 279-284, 357, 369, 372, 382, and 458), AMP binding site (residues 140, 180-181, 227, 229-230, 233, 257-258, 279-284, 357, 369, 372, 379-382, and 439), and CoA binding site (residues 180, 229-230, 233, 257, 379-381, 433, and 439).

15. The genetically modified host cell of claim 1, wherein the 2-pyrrolidone synthase comprises an amino acid sequence having at least 90% identity with SEQ ID NO:1.

16. The genetically modified host cell of claim 14, wherein the 2-pyrrolidone synthase comprises an amino acid sequence having at least 95% identity with SEQ ID NO:1.

17. The genetically modified host cell of claim 15, wherein the 2-pyrrolidone synthase comprises an amino acid sequence having at least 99% identity with SEQ ID NO:1.

* * * * *